(12) United States Patent
Grigoryants et al.

(10) Patent No.: US 7,625,346 B2
(45) Date of Patent: Dec. 1, 2009

(54) TRANSBRONCHIAL NEEDLE ASPIRATION DEVICE

(75) Inventors: Sergey S. Grigoryants, Arlington, MA (US); Luis J. Maseda, Cambridge, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 406 days.

(21) Appl. No.: 10/449,826

(22) Filed: May 30, 2003

(65) Prior Publication Data

US 2004/0243023 A1 Dec. 2, 2004

(51) Int. Cl.
*A61B 10/00* (2006.01)

(52) U.S. Cl. ............... 600/567; 600/564; 600/565; 600/566; 600/568; 600/569; 600/570; 600/571

(58) Field of Classification Search .......... 600/564–571
See application file for complete search history.

(56) References Cited

U.S. PATENT DOCUMENTS

| | | | |
|---|---|---|---|
| 1,087,845 A | | 2/1914 | Stevens |
| 4,249,541 A | * | 2/1981 | Pratt .................. 600/566 |
| 4,532,935 A | | 8/1985 | Wang |
| 4,605,011 A | | 8/1986 | Näsland |
| 4,617,940 A | | 10/1986 | Wang |
| 4,693,257 A | | 9/1987 | Markham |
| 4,702,260 A | | 10/1987 | Wang |
| 4,763,667 A | | 8/1988 | Manzo |

(Continued)

FOREIGN PATENT DOCUMENTS

DE 10034297 A1 4/2001

(Continued)

OTHER PUBLICATIONS

Seijo et al., "Interventional Pulmonology," N Eng J Med, 344 (10) : 740-9 (Mar. 8, 2001).

(Continued)

*Primary Examiner*—Max Hindenburg
*Assistant Examiner*—Jeffrey G Hoekstra
(74) *Attorney, Agent, or Firm*—Kriegsman & Kriegsman

(57) ABSTRACT

Transbronchial needle aspiration (TBNA) device. In one embodiment, the device comprises a handle and a flexible catheter, the handle having a bore, the proximal end of the catheter being fixed within the handle bore. A protective tubular hub having a flared distal end is press-fit coaxially within the distal end of the catheter, the distal end of the catheter being sealed around the distal end of the hub so as to define a distal opening. A hollow needle having a sharp tip at its distal end is disposed within the catheter, the needle tip being sized for insertion through the distal opening of the catheter. The distal end of a flexible wire is coupled to the proximal end of the needle, the proximal end of the wire extending through the handle bore and coupled to a button slide accessible through a slot in the handle. The button slide is movable between a distal position in which the needle tip extends through the distal opening of the catheter and a proximal position in which the needle tip is disposed within the hub. When in either its distal position or its proximal position, a pawl on the button slide releasably engages a corresponding notch on the handle to lock the button slide in place.

16 Claims, 25 Drawing Sheets

U.S. PATENT DOCUMENTS

| | | | |
|---|---|---|---|
| 4,766,906 A | 8/1988 | Wang | |
| 4,766,907 A | 8/1988 | de Groot et al. | |
| 4,791,937 A | 12/1988 | Wang | |
| 4,799,494 A | 1/1989 | Wang | |
| 4,881,551 A | 11/1989 | Taylor | |
| 4,890,626 A | 1/1990 | Wang | |
| 4,893,635 A | 1/1990 | de Groot et al. | |
| 4,907,599 A | 3/1990 | Taylor | |
| 4,911,690 A | 3/1990 | Mulshine et al. | |
| 4,966,162 A | 10/1990 | Wang | |
| 4,982,739 A | 1/1991 | Hamstreet et al. | |
| 4,989,614 A | 2/1991 | Dejter, Jr. et al. | |
| 5,036,860 A | 8/1991 | Leigh et al. | |
| 5,056,529 A | 10/1991 | de Groot | |
| 5,081,999 A | 1/1992 | Hamstreet et al. | |
| 5,172,701 A | 12/1992 | Leigh | |
| 5,213,110 A | 5/1993 | Kedem et al. | |
| 5,297,560 A | 3/1994 | Meduri | |
| 5,320,110 A | 6/1994 | Wang | |
| 5,335,671 A | 8/1994 | Clement | |
| 5,409,013 A | 4/1995 | Clement | |
| 5,423,330 A | 6/1995 | Lee | |
| 5,474,075 A | 12/1995 | Goldberg et al. | |
| 5,511,556 A | 4/1996 | DeSantis | |
| 5,560,373 A | 10/1996 | DeSantis | |
| 5,571,091 A | 11/1996 | Davis et al. | |
| 5,601,588 A | 2/1997 | Tonomura et al. | |
| 5,669,394 A | 9/1997 | Bergey et al. | |
| 5,713,368 A | 2/1998 | Leigh | |
| 5,779,646 A | 7/1998 | Koblish | |
| 5,817,033 A | 10/1998 | DeSantis et al. | |
| 5,817,073 A | 10/1998 | Krespi | |
| 5,840,059 A * | 11/1998 | March et al. | 604/509 |
| 5,843,091 A | 12/1998 | Madsen et al. | |
| 5,964,716 A | 10/1999 | Gregoire et al. | |
| 5,971,939 A | 10/1999 | DeSantis et al. | |
| 5,987,353 A | 11/1999 | Khatchatrian | |
| 6,056,700 A | 5/2000 | Burney et al. | |
| 6,083,176 A | 7/2000 | Terwilliger | |
| 6,106,484 A | 8/2000 | Terwilliger | |
| 6,174,307 B1 | 1/2001 | Daniel et al. | |
| 6,193,673 B1 | 2/2001 | Viola et al. | |
| 6,228,039 B1 | 5/2001 | Binmoeller | |
| 6,248,081 B1 | 6/2001 | Nishtalas | |
| 6,283,925 B1 | 9/2001 | Terwilliger | |
| 6,436,054 B1 * | 8/2002 | Viola et al. | 600/562 |
| 6,454,702 B1 | 9/2002 | Smith | |
| 2001/0004676 A1 | 6/2001 | Ouchi | |
| 2001/0005778 A1 | 6/2001 | Ouchi | |
| 2002/0022788 A1 | 2/2002 | Corvi et al. | |
| 2003/0097079 A1 | 5/2003 | Garcia | |

FOREIGN PATENT DOCUMENTS

| | | |
|---|---|---|
| WO | WO 99/59475 A1 | 11/1999 |
| WO | WO 01/12072 A1 | 2/2001 |
| WO | WO 02/07603 A1 | 1/2002 |

OTHER PUBLICATIONS

Dasgupta et al., Utility of Transbronchial Needle Aspiration in the Diagnosis of Endobronchial.

Lesions, Chest, 115:1237-41 (1999).

Dasgupta et al., "Transbronchial Needle Aspiration," Clinics in Chest Medicine, 20(1):39-51 (Mar. 1999).

Haponik et al., "Underutilization of Transbronchial Needle Aspiration," Chest, 112:251-3 (1997).

* cited by examiner

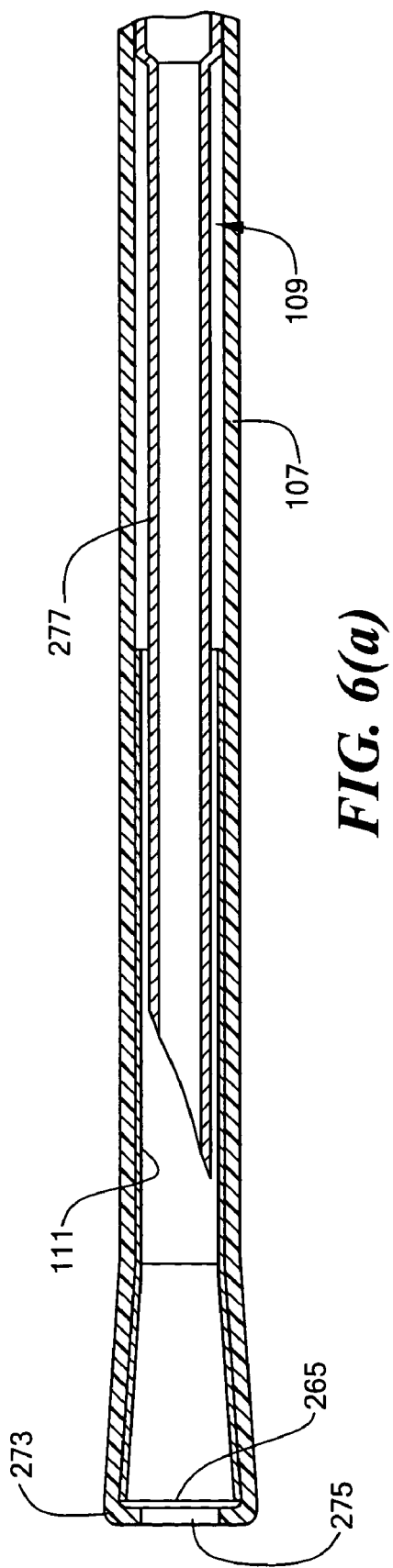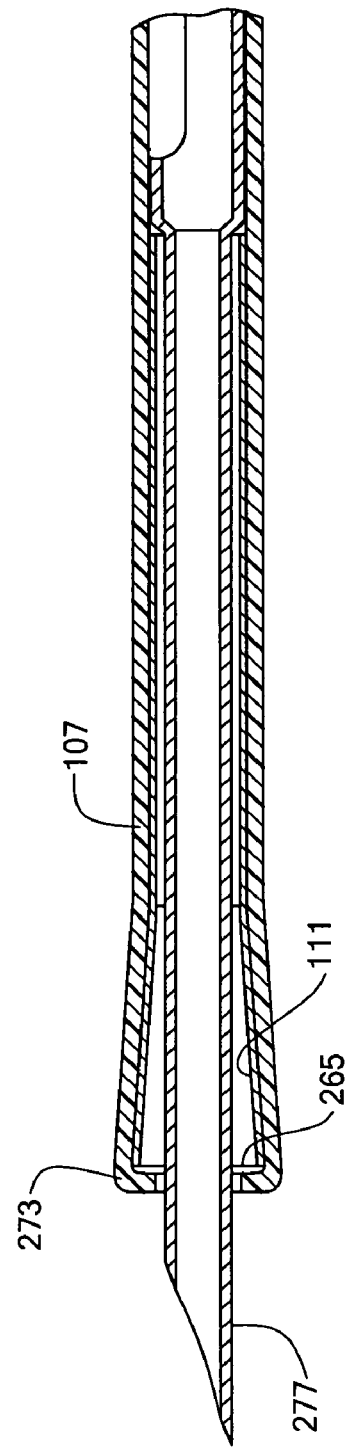
FIG. 6(a)
FIG. 6(b)

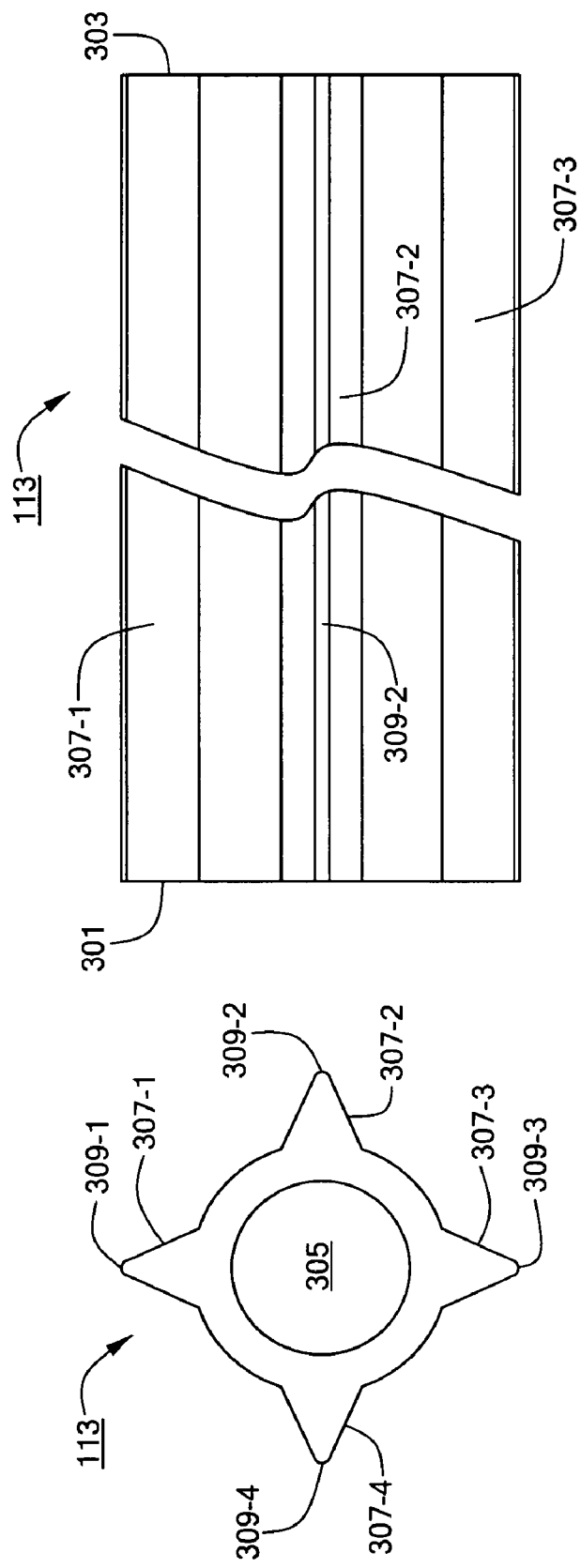

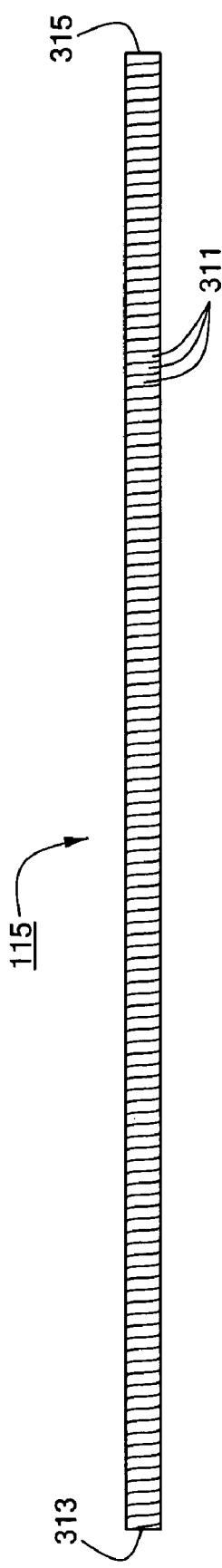
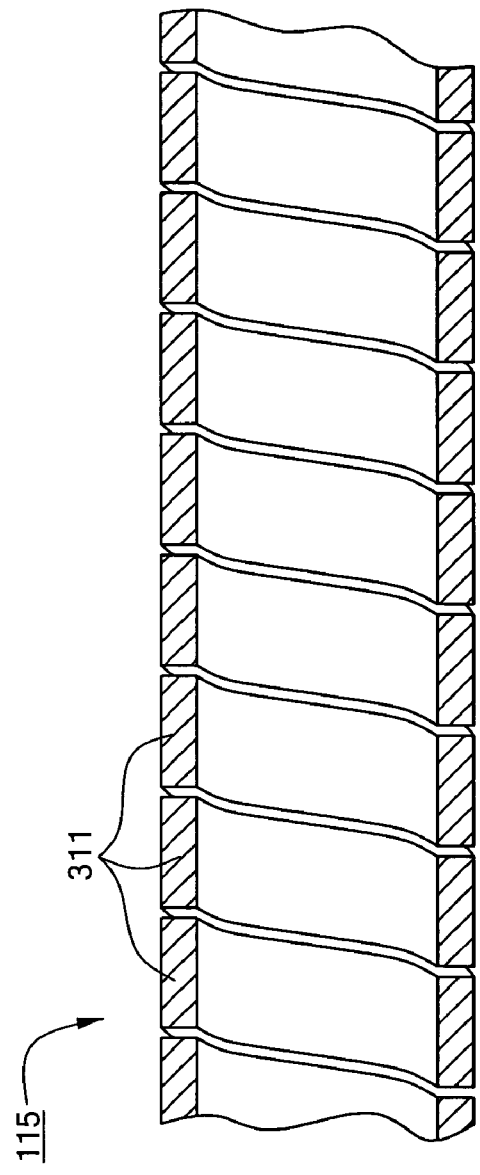
FIG. 15(a)
FIG. 15(b)

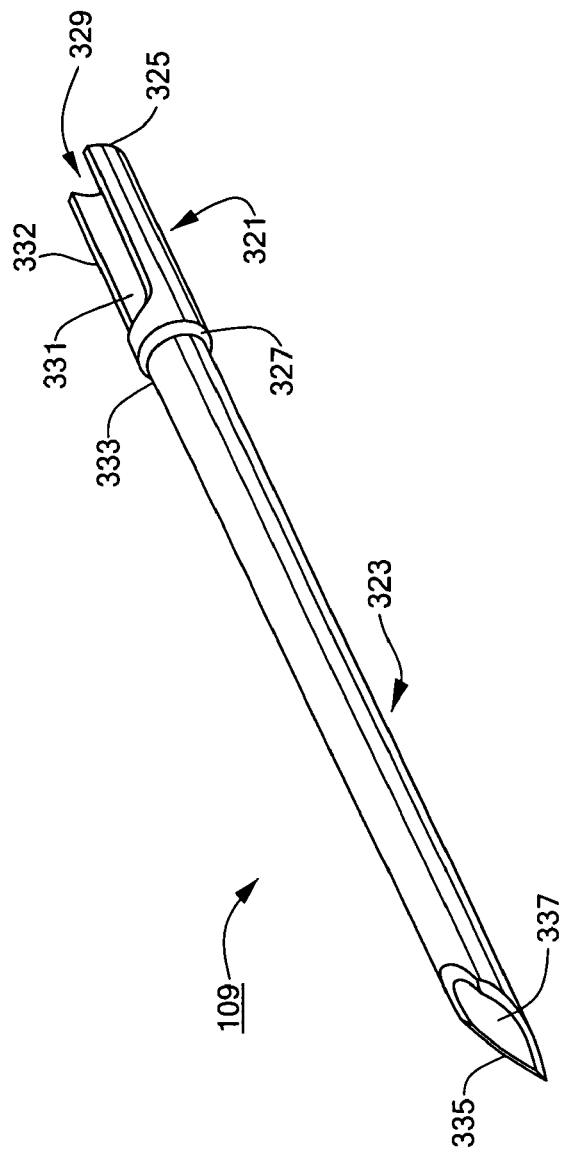
FIG. 17(a)
FIG. 17(b)

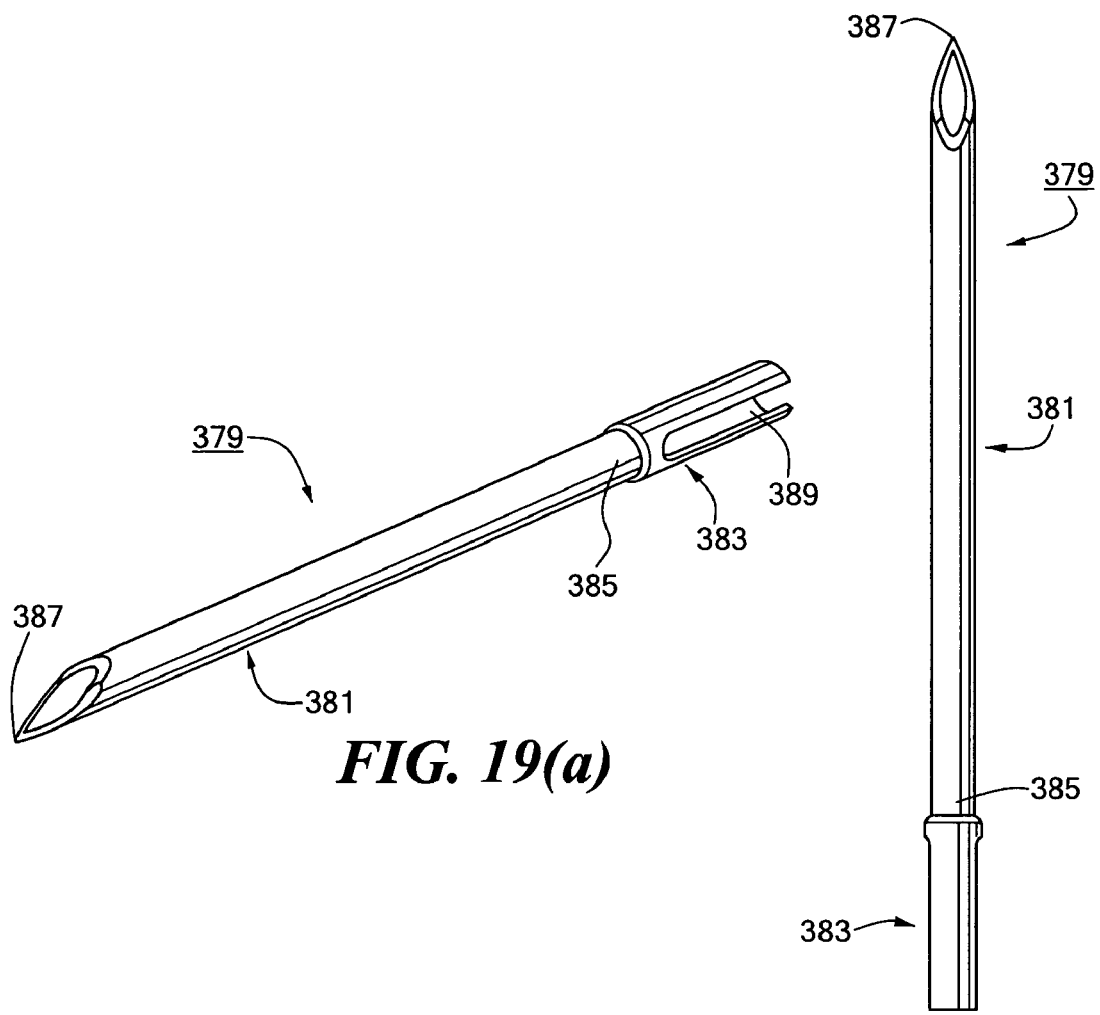
*FIG. 19(a)*
*FIG. 19(c)*
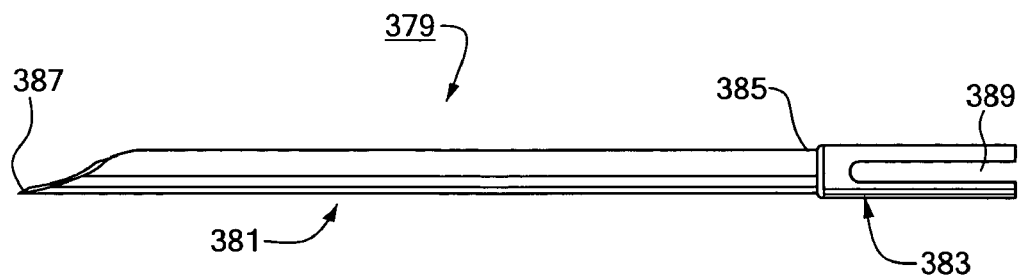
*FIG. 19(b)*

TRANSBRONCHIAL NEEDLE ASPIRATION DEVICE

BACKGROUND OF THE INVENTION

The present invention relates generally to tissue sampling devices and relates more particularly to transbronchial needle aspiration devices.

In order to diagnose and to stage lung cancer in a patient, it is often necessary to biopsy a tissue sample from a nearby lymph node of the patient. One type of technique that has been used in the past to obtain such a tissue sample involves percutaneously inserting a sampling needle through the patient's chest into the patient's lung and then through the bronchial wall of the lung into a nearby lymph node. Examples of devices adapted for percutaneous tissue sampling are disclosed in the following U.S. patents, all of which are incorporated herein by reference: U.S. Pat. No. 5,971,939, inventors DeSantis et al., which issued Oct. 26, 1999; U.S. Pat. No. 5,713,368, inventor Leigh, which issued Feb. 3, 1998; U.S. Pat. No. 4,799,494, inventor Wang, which issued Jan. 24, 1989; and U.S. Pat. No. 4,766,907, inventors de Groot et al., which issued Aug. 30, 1988.

Although the above-described percutaneous sampling technique has proven satisfactory in terms of time and expense, such a technique does have its shortcomings. One such shortcoming is the risk of uncontrollable bleeding if the biopsy needle, which may be quite large in diameter, pierces or shears a blood vessel. Another shortcoming is the risk of pneumothorax, i.e., lung collapse, resulting from the puncturing of the lung by the biopsy needle, causing air to leak from the lung and to accumulate between the lung surface and the chest cage. In fact, if pneumothorax is severe enough, the patient may require a chest tube to drain air from the chest cavity. Moreover, in extreme cases, the condition may be fatal. Still another shortcoming is the risk of infection resulting from the percutaneous insertion of the needle into the patient.

Accordingly, another technique that has been used to obtain a lymph node tissue sample is transbronchial needle aspiration (sometimes referred to as "TBNA"). In transbronchial needle aspiration, the distal end of a bronchoscope is inserted through a patient's mouth and to a neutral location within the patient's lung, the proximal end of the bronchoscope not being inserted into the patient and, instead, extending externally thereto. The distal end of a TBNA device is then inserted through a working channel of the bronchoscope, the proximal end of the TBNA device not being inserted into the bronchoscope and, instead, extending externally to the patient. The TBNA device typically comprises a catheter, a wire longitudinally disposed within the catheter, a histology sampling needle coupled to the distal end of the wire, a cap coupled to the proximal end of the wire and accessible externally to the patient for moving the wire relative to the catheter so as to alternately extend the needle beyond the distal end of the catheter and retract the needle into the catheter, and a port accessible externally to the patient for coupling a syringe to the proximal end of the catheter so that the syringe may provide suction to the catheter.

The TBNA device is typically loaded into a bronchoscope with its needle in a retracted position and with a syringe attached to the port. Once confirmation is received that the distal end of the TBNA device has passed entirely through the bronchoscope (such confirmation typically being provided using a video channel of the same bronchoscope), the bronchoscope and the TBNA device are advanced together to the target site, and the needle is advanced to its extended position. The needle is then inserted through the bronchial wall of the patient and into a nearby lymph node. At this time, the syringe is used to apply suction. In the unfortunate event that the needle errantly penetrates a blood vessel, instead of a lymph node, the application of suction causes blood to be aspirated into the catheter and the syringe, where it is detected. In such a case, the application of suction is discontinued and the bloodied TBNA device is removed from the bronchoscope and the patient. A fresh TBNA device is then loaded into the bronchoscope and the patient in the manner described above, and another attempt is made to penetrate the lymph node.

If, while suction is applied, it appears that the sampling needle has penetrated a lymph node, as is desired, the catheter is agitated to help shear tissue from the penetrated lymph node into the sampling needle. With a tissue sample thus disposed within the sampling needle, the needle is retracted into the catheter. The TBNA device is then removed from the bronchoscope and the patient. The needle is then advanced out of the catheter, and negative suction is then used to expel the tissue from the sampling needle onto a slide or the like for histological examination.

Examples of TBNA devices are disclosed in the following patents, all of which are incorporated herein by reference: U.S. Pat. No. 5,056,529, inventor de Groot, which issued Oct. 15, 1991; U.S. Pat. No. 4,966,162, inventor Wang, which issued Oct. 30, 1990; U.S. Pat. No. 4,890,626, inventor Wang, which issued Jan. 2, 1990; U.S. Pat. No. 4,791,937, inventor Wang, which issued Dec. 20, 1988; U.S. Pat. No. 4,766,906, inventor Wang, which issued Aug. 30, 1988; U.S. Pat. No. 4,702,260, inventor Wang, which issued Oct. 27, 1987 U.S. Pat. No. 4,693,257, inventor Markham, which issued Sep. 15, 1987; U.S. Pat. No. 4,617,940, inventor Wang, which issued Oct. 21, 1986; U.S. Pat. No. 4,532,935, inventor Wang, which issued Aug. 6, 1985; and U.S. Pat. No. 4,249,541, inventor Pratt, which issued Feb. 10, 1981.

Referring now to FIGS. 1 and 2, there are shown perspective and enlarged fragmentary section views, respectively, of a conventional, commercially available embodiment of a TBNA device, said TBNA device being represented generally by reference numeral 11.

Device 11 comprises a handle or body 13. Body 13 is a branched or T-shaped, tubular member shaped to include a first port 15 at its proximal end, a second port 17 at its distal end, and a third port 19 extending perpendicularly to and between said first port 15 and said second port 17. Each of first port 15, second port 17 and third port 19 is in fluid communication with the other two ports. Third port 19 is adapted to receive a syringe for use in providing suction to device 11.

Device 11 also comprises a flexible catheter 21. Catheter 21 has a proximal end and a distal end 23, the proximal end of catheter 21 being fixedly mounted within second port 17.

Device 11 additionally comprises a metal hub or tip 25. Tip 25 is a generally tubular member having a proximal end 27 and a distal end 29. A plurality of external barbs 31 are formed on tip 25 intermediate to proximal end 27 and distal end 29. Proximal end 27 and barbs 31 are mounted within catheter 21 proximate to distal end 23, with distal end 29 of tip 25 not being inserted into catheter 21, but rather, externally abutting distal end 23 of catheter 21.

Device 11 further comprises a flexible wire 35, wire 35 having a proximal end 37 and a distal end 39. Proximal end 37 of wire 35 is fixed to a cap 41, cap 41 being adapted to be screwed onto first port 15 of body 13. The remainder of wire 35 is threaded through ports 15 and 17 of body 13 and into catheter 21, with distal end 39 of wire 35 being disposed within catheter 21 proximate to distal end 23. A stop (not shown) is provided on wire 35, said stop being engageable with body 13 to delimit proximal movement of wire 35.

Device 11 also comprises a histology sampling needle 51, needle 51 having a proximal end 53 and a distal end 55. Proximal end 53 of needle 51 is fixed to distal end 39 of wire 35. Distal end 55 of needle 51 is shaped to include a sharp tip. A bore 57 extends proximally from distal end 55 of needle 51 to a side opening 59 proximate to proximal end 53. An annular seal 61 is mounted over needle 51 just distal to side opening 59, seal 61 being adapted to abut proximal end 27.

Device 11 may be used essentially in the fashion described above to obtain a tissue sample. To place needle 51 in its advanced position, i.e., so that distal end 55 of needle 51 extends beyond tip 25, one moves cap 41 distally and screws cap 41 onto port 15. Conversely, to withdraw or to retract needle, i.e., so that distal end 53 of needle 51 is disposed within tip 25, one unscrews cap 41 from port 15 and moves cap 41 proximally relative to body 13 until restrained by the aforementioned stop.

Although device 11 is satisfactory in many respects, the present inventors have identified certain shortcomings therewith. One such shortcoming is that, whereas device 11 includes means for retaining needle 51 in its extended position (namely, by screwing cap 41 onto port 15), device 11 does not include corresponding means for retaining needle 51 in a retracted position. Consequently, if one wishes to ensure that needle 51 is not advanced through distal end 23 of catheter 21 at an inopportune moment, one must constantly pull cap 41 proximally relative to body 13. However, as can readily be appreciated, such a requirement substantially complicates the manipulation of device 11, especially by an individual operator.

Another shortcoming identified by the present inventors with device 11 is the branched shape of body 13 and the resultant orientation of a syringe coupled thereto through port 19. More specifically, the present inventors have found that the perpendicular orientation of a syringe relative to the longitudinal axis of catheter 21 makes device 11 cumbersome and difficult to manipulate by an individual operator.

Yet another shortcoming identified by the present inventors with device 11 is that, when needle 51 is in its extended position and a load force is applied to the distal end 53 of needle 51 (such as is the case when needle 51 is used to penetrate a tissue), needle 51 tends to be moved proximally relative to catheter 21, thereby effectively shortening the usable length of needle 51 for penetrating the tissue. Such a loss in the usable length of needle 51 occurs because wire 35 has an outer diameter that is considerably smaller than the inner diameter of catheter 21, giving wire 35 room to move laterally within catheter 21. Consequently, when catheter 21 is bent, as is the case when device 11 is deployed in a patient, and a load force is applied to needle 51, wire 35 tends to take the longest possible path through catheter 21.

Conversely, when cap 41 is pulled back relative to catheter 21 to its fully retracted position and catheter 21 is bent to a substantial degree, needle 51 may not fully retract relative to catheter 21. This is because of the aforementioned difference between the outer diameter of wire 35 and the inner diameter of catheter 21 and the tendency of wire 35 to take the shortest possible path through catheter 21. As can readily be appreciated, if needle 51 cannot be fully retracted when sampling is not being performed, damage may occur to equipment, operators and/or the patient.

Still another shortcoming identified by the present inventors with device 11 is that tip 25 is susceptible to becoming dislodged distally from catheter 21. As can readily be appreciated, if tip 25 were to become separated from catheter 21, the risks to the patient would be considerable. Such a susceptibility of tip 25 to becoming dislodged is due, in part, to the fact that tip 25 is held within catheter 21 only by the friction-fit of catheter 21 over barbs 31 and proximal end 27. This susceptibility is exacerbated by the fact that, when needle 51 is advanced to its extended position, seal 61 applies a distally directed force against tip 25. In addition, because catheter 21 has a tendency to bulge radially outwardly in the area where it overlies barbs 31, this bulged area of catheter 21 is susceptible to becoming snagged on the distal end of a bronchoscope when device 11 is retracted into the bronchoscope. Such snagging results in additional distally directed force being applied to tip 25 relative to catheter 21.

Still yet another shortcoming identified by the present inventors with device 11 is that distal end 29 of tip 25, which is not disposed within catheter 21, but rather, lies externally thereto, has a tendency to scratch and, thus, to damage the working channel of a bronchoscope.

Still a further shortcoming identified by the present inventors with device 11 is that, when needle 51 is retracted, distal end 55 of needle 51 has a tendency to be withdrawn proximally from hub 25. This requires needle 51 to be re-aligned properly with hub 25 in order for needle 51 to be re-inserted into hub 25.

Still yet a further shortcoming identified by the present inventors with device 11 is that seal 61 often does not create an air-tight seal against tip 25 when needle 51 is placed in its fully extended position; as a result, the full extent of the vacuum force applied to bore 57 of needle 51 by the syringe is frequently not experienced.

SUMMARY OF THE INVENTION

It is an object of the present invention to provide a tissue sampling device suitable for use in transbronchial needle aspiration (TBNA).

It is another object of the present invention to provide a tissue sampling device as described above that overcomes at least some of the shortcomings associated with existing TBNA devices.

It is still another object of the present invention to provide a device as described above that can be mass-produced relatively inexpensively, that has a minimal number of parts, and that is easy to operate.

In furtherance of the above and other objects to be described or to become apparent from the description below, there is provided, according to one aspect of the invention, a tissue sampling device suitable for use in transbronchial needle aspiration, said tissue sampling device comprising (a) a flexible catheter, said flexible catheter having a proximal end and a distal end; (b) a sampling needle, said sampling needle being insertable into said flexible catheter and being shaped to include a distal tip; (c) means coupled to said sampling needle for moving said sampling needle between a first position wherein said distal tip of said sampling needle is disposed within said flexible catheter and a second position wherein said distal tip of said sampling needle extends distally beyond said distal end of said flexible catheter; and (d) means for retaining said sampling needle at said first position in a releasably locked fashion.

According to another aspect of the invention, there is provided a tissue sampling device suitable for use in transbronchial needle aspiration, said tissue sampling device comprising (a) a flexible catheter, said flexible catheter having a proximal end and a distal end; (b) a sampling needle, said sampling needle being disposed at said distal end of said flexible catheter and having a distal tip; and (c) a handle assembly, said handle assembly being secured to said proximal end of said flexible catheter, said handle assembly including a port adapted to receive a syringe in such a manner as to fluidly interconnect said syringe to said flexible catheter, said port being oriented parallel to said proximal end of said flexible catheter.

According to yet another aspect of the invention, there is provided a tissue sampling device suitable for use in transbronchial needle aspiration, said tissue sampling device comprising (a) a flexible catheter, said flexible catheter having a proximal end, a distal end and an inner diameter; (b) a wire, said wire extending substantially coaxially within said flexible catheter, said wire having a proximal end, a distal end and an outer diameter, said outer diameter of said wire being substantially less than said inner diameter of said flexible catheter; (c) a sampling needle, said sampling needle being positioned at said distal end of said flexible catheter and being coupled to said distal end of said wire; (d) means inserted over at least a portion of said wire for centering said wire within said flexible catheter while still providing a space for fluid flow; and (e) a handle assembly, said flexible catheter being fixed at said proximal end to said handle assembly.

According to still yet another aspect of the invention, there is provided a tissue sampling device suitable for use in transbronchial needle aspiration, said tissue sampling device comprising (a) a flexible catheter, said flexible catheter having a proximal end and a distal end; (b) a hub, said hub being substantially tubular and having a proximal end and a distal end, said hub being disposed within said flexible catheter, with said distal end of said flexible catheter being inverted so as to retain said hub distally within said flexible catheter; (c) a sampling needle, said sampling needle having a tip; and (d) means coupled to said sampling needle for moving said sampling needle between a first position wherein said tip of said sampling needle is disposed within said hub and a second position wherein said tip of said sampling needle extends distally beyond said distal end of said flexible catheter.

According to a further aspect of the invention, there is provided a tissue sampling device suitable for use in transbronchial needle aspiration, said tissue sampling device comprising (a) a flexible catheter, said flexible catheter having a proximal end, a distal end and an inner diameter; (b) a wire, said wire extending within said flexible catheter, said wire having a proximal portion and a distal portion, said distal portion having a decreased thickness as compared to said proximal portion; (c) a sampling needle, said sampling needle being positioned at said distal end of said flexible catheter and being coupled to said wire; and (d) a compressed spring surrounding and secured to at least a portion of said distal portion of said wire.

According to still a further aspect of the invention, there is provided a tissue sampling device suitable for use in transbronchial needle aspiration, said tissue sampling device comprising (a) a handle, said handle comprising a body and a cover, said body and said cover together defining a top, a bottom and a distal end, said top having a slot, said distal end having a bore; (b) a button slide, said button slide being slidably mounted in said handle and including a button, said button extending upwardly through said slot for manipulation by an operator; (c) a flexible catheter, said flexible catheter having a proximal end and a distal end, said proximal end being mounted within said bore in said handle; (d) a wire, said wire having a proximal end and a distal end, said proximal end of said wire being coupled to said button slide; and (e) a sampling needle, said sampling needle being coupled to said distal end of said wire, said sampling needle having a distal tip; (f) wherein said button slide is movable between a first position in which said distal tip of said sampling needle is positioned within said flexible catheter and a second position in which said distal tip of said sampling needle extends distally past said proximal end of said flexible catheter.

According to still yet a further aspect of the invention, there is provided a tissue sampling device suitable for use in transbronchial needle aspiration, said tissue sampling device comprising (a) a flexible catheter, said flexible catheter having a proximal end and a distal end; (b) a hub, said hub being substantially tubular and having a proximal end and a distal end, said hub being disposed within said flexible catheter proximate to said distal end thereof; (c) a sampling needle, said sampling needle having a distal tip and a shoulder; and (d) means coupled to said sampling needle for moving said sampling needle between a first position wherein said distal tip of said sampling needle is disposed within said hub and a second position wherein said distal tip of said sampling needle extends distally beyond said distal end of said flexible catheter; (e) wherein said shoulder of said sampling needle is adapted to directly abut said proximal end of said hub to form a seal therewith when said sampling needle is placed in said second position.

For purposes of the present specification and claims, various relational terms like "top," "bottom," "proximal," "distal," "upper," "lower," "front," and "rear" are used to describe the present invention when said invention is positioned in a given orientation. It is to be understood that, by altering the orientation of the invention, certain relational terms may need to be adjusted accordingly.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts:

FIGS. 6(a) and 6(b) are fragmentary section views of the TBNA device of FIG. 3, showing the distal portion thereof with the needle in its retracted and extended positions, respectively;

FIGS. 14(a) and 14(b) are proximal and side views, respectively, of the jacket shown in FIG. 3;

FIGS. 15(a) and 15(b) are right side and enlarged right longitudinal section views, respectively, of the spring shown in FIG. 3;

FIGS. 17(a) through 17(d) are perspective, left side, top and enlarged fragmentary left longitudinal section views, respectively, of the needle shown in FIG. 3;

FIGS. 19(a) through 19(c) are perspective, top and left side views, respectively, of a second alternate needle.

DETAILED DESCRIPTION OF PREFERRED EMBODIMENTS

Figure 1:
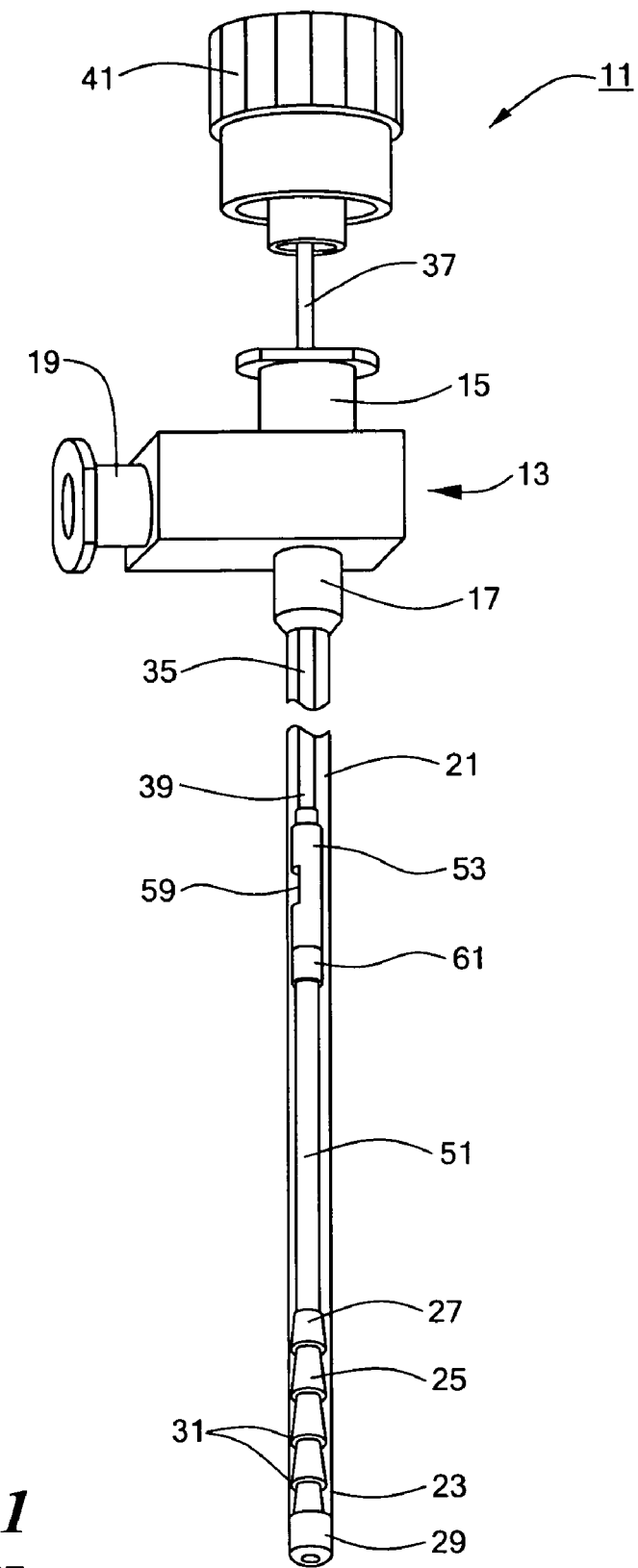
FIG. 1 is a perspective view of a conventional transbroncial needle aspiration (TBNA) device.
Figure 2:
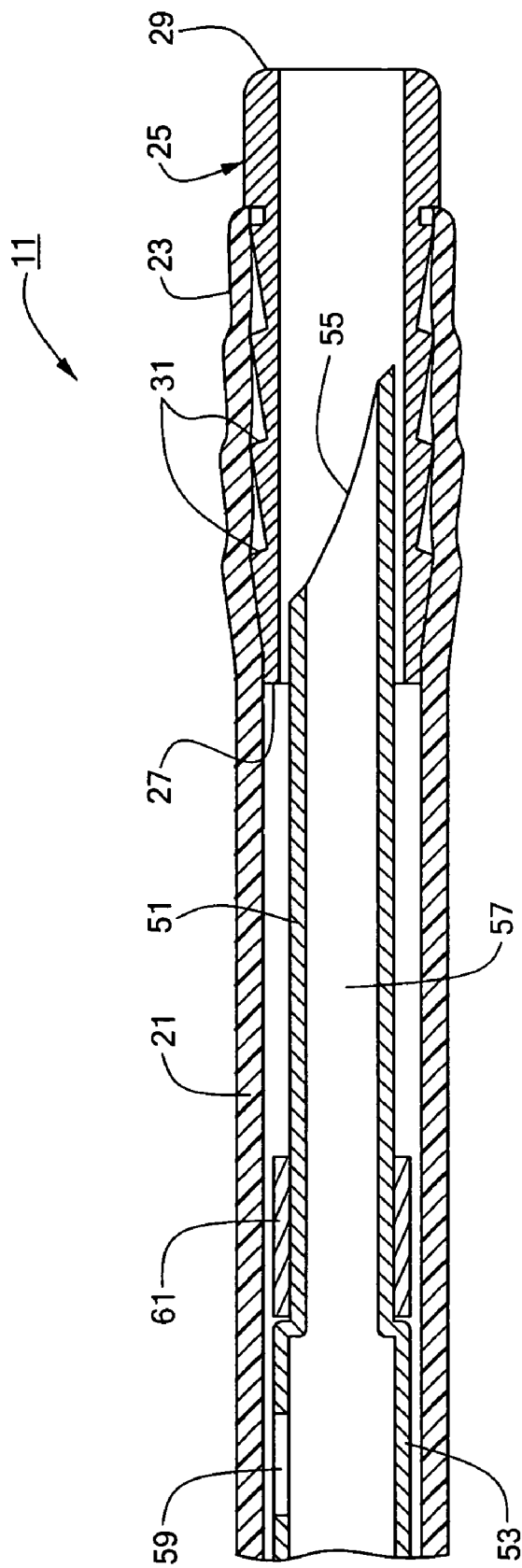
FIG. 2 is a fragmentary, section view of the TBNA device of FIG. 1, showing the distal portion thereof.
Figure 3:
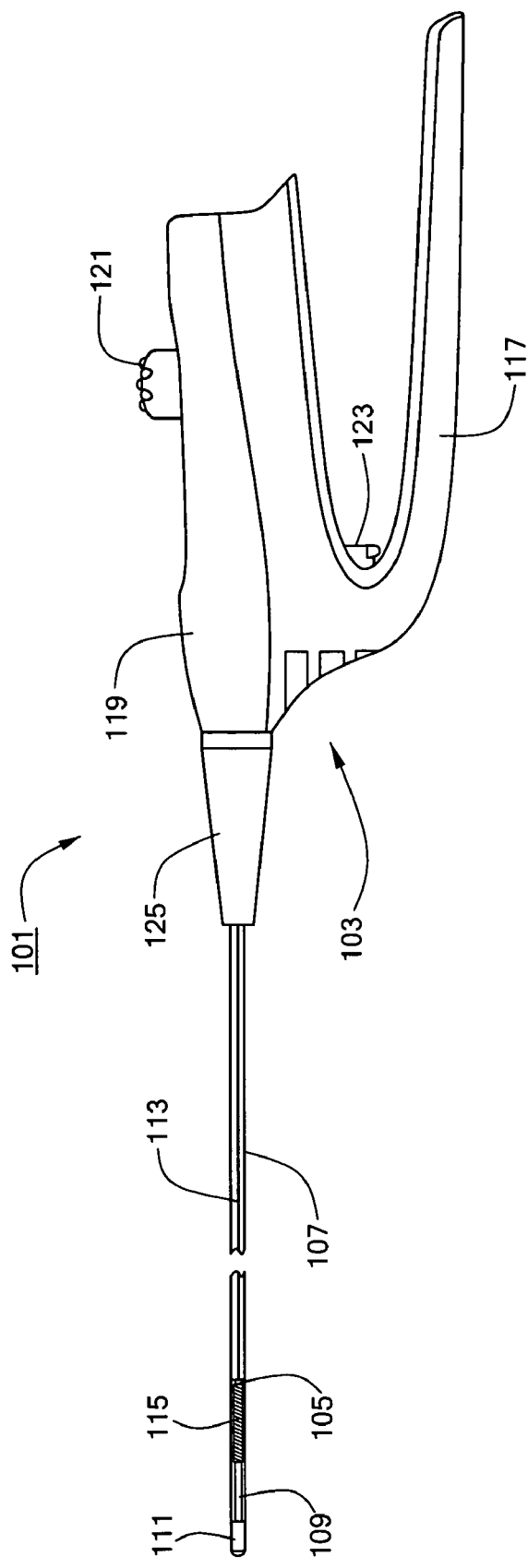
FIG. 3 is a side view of one embodiment of a TBNA device constructed according to the teachings of the present invention, the TBNA device being shown with its needle in the retracted position.
Figure 4:
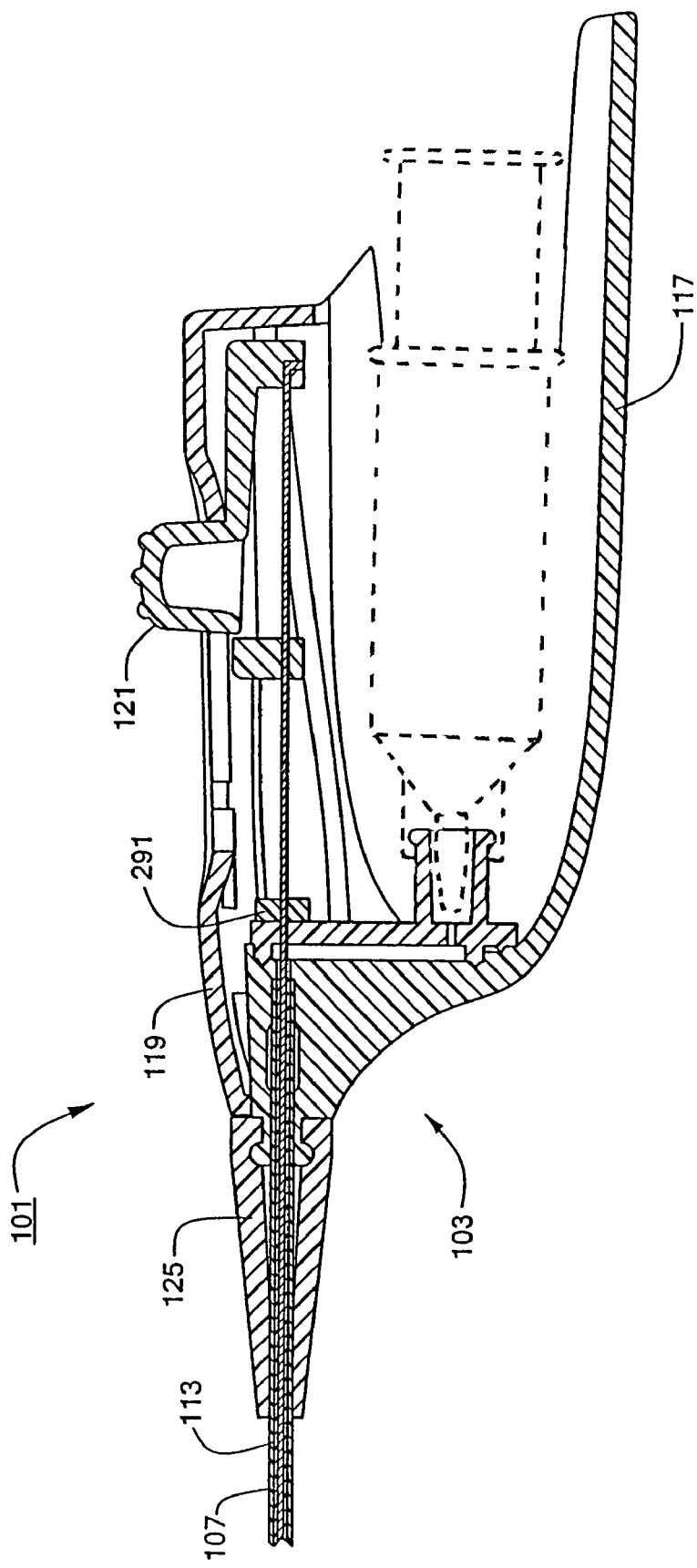
FIG. 4 is a fragmentary longitudinal section view of the TBNA device of FIG. 3, the TBNA device being shown with its needle in the retracted position and shown with a syringe (in phantom) attached thereto.
Figure 5:
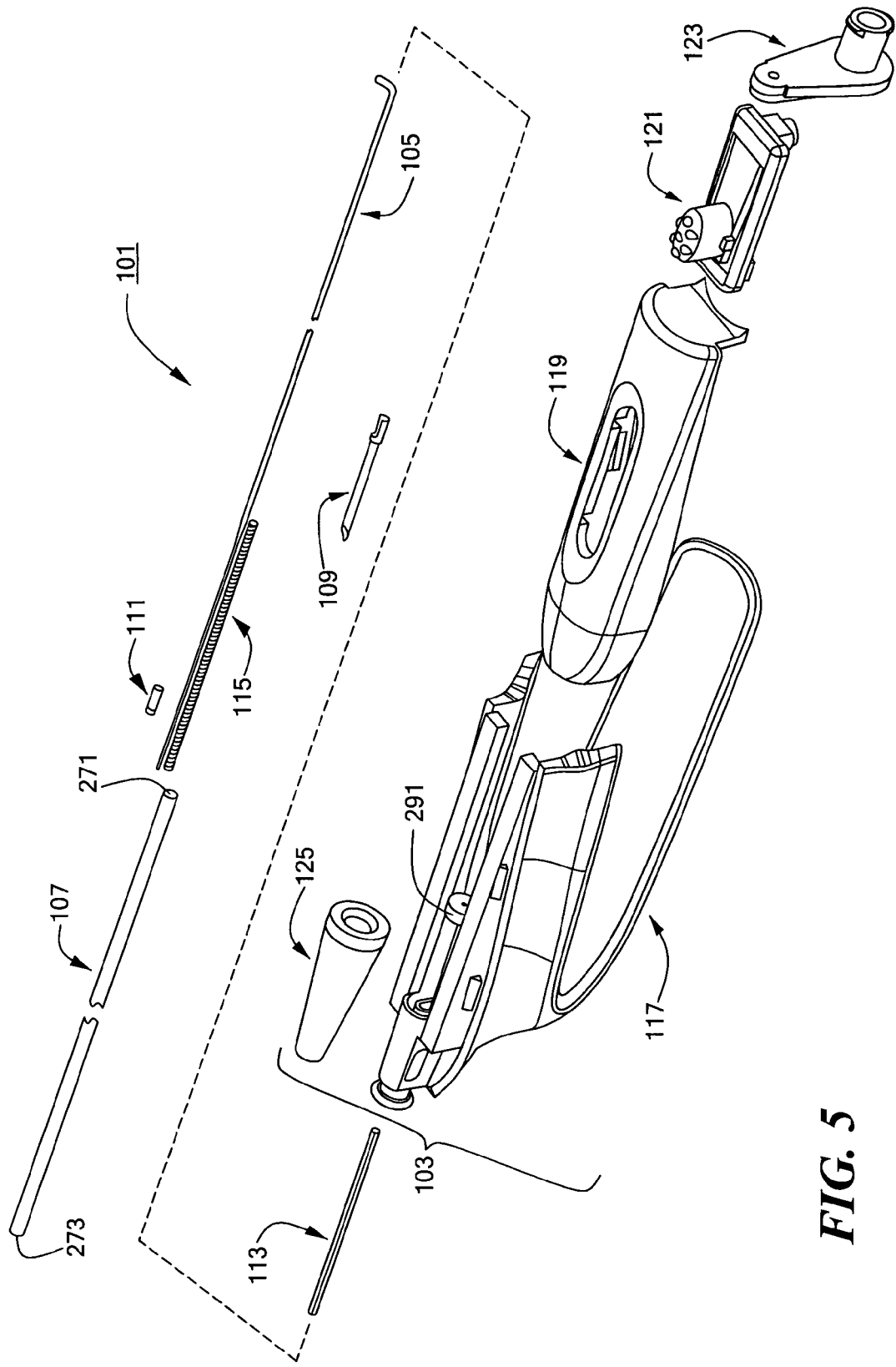
FIG. 5 is an exploded perspective view of the TBNA device of FIG. 3.

Referring now to FIGS. 3, 4, 5, 6(a) and 6(b), there are shown various views, respectively, of one embodiment of a transbronchial needle aspiration (TBNA) device constructed according to the teachings of the present invention, said TBNA device being represented generally by reference numeral 101.

Device 101 comprises a handle assembly 103, a wire 105, a flexible catheter 107, a sampling needle 109, a hub 111, a jacket 113 and a spring 115.

Handle assembly 103, in turn, comprises a body 117, a cover 119, a button slide 121, a syringe connector 123 and a strain relief member 125.

Referring now to FIGS. 7(a) through 7(f), body 117 is a unitary, generally C-shaped member, preferably made of a durable molded plastic or another similarly suitable material, comprising a top portion 131, a distal end portion 133 and a bottom portion 135, the sides and proximal end of body 117 being open. Top portion 131, distal end portion 133 and bottom portion 135 collectively define a longitudinally-extending cavity 139, which, as will be described below, is shaped to accommodate a syringe or similar aspirating device.

Top portion 131 is shaped to include a pair of rails 141-1 and 141-2, rails 141-1 and 141-2 being separated by a slot 142 whose purpose will become apparent below. A first pair of detents 143-1 and 143-2 are formed on the outer side surface of rail 141-1, and a second pair of detents 145-1 and 145-2 are formed on the outer side surface of rail 141-2, second detents 145-1 and 145-2 being staggered relative to first detents 143-1 and 143-2. As will be described below, detents 143-1, 143-2, 145-1 and 145-2 are used in the coupling together of body 117 and cover 119 to form a handle.

Distal end portion 133 includes a proximal surface 147, proximal surface 147 being shaped to receive syringe connector 123. Distal end portion 133 also includes a distally extending post 149. A bore 151 (which is seen best in FIG. 7(f)) extends longitudinally through post 149 and continues through the remainder of distal end portion 133 to cavity 139. Bore 151 includes a distal portion 151-1 of comparatively greater cross-sectional diameter and a proximal portion 151-2 of comparatively lesser cross-sectional diameter, distal portion 151-1 extending for most of the length of bore 151. As will be described further below, distal portion 151-1 is sized to securely receive the proximal end of catheter 107, with the proximal end of wire 105 passing through proximal portion 151-2. A transverse opening 153 is also provided in distal end portion 133, transverse opening 153 intersecting distal portion 151-1 of bore 151 at an intermediate location thereof.

Bottom portion 135 has a top surface 155 and a bottom surface 157. Top surface 155 is contoured to receive a syringe or similar aspirating device thereon. Bottom surface 157 is contoured to fit ergonomically within the hand of an operator.

Referring now to FIGS. 8(a) through 8(e), cover 119 is a unitary, generally trough-shaped member, preferably made of a durable molded plastic or another similarly suitable material, comprising a top portion 161, a pair of side portions 163-1 and 163-2, and a proximal end portion 165, the bottom and the distal end of cover 119 being open. Top portion 161 is shaped to include an elongated, longitudinally-extending slot 167, through which, as will be further described below, the button portion of button slide 121 is adapted to extend. Top portion 161 is also shaped to include a proximal pair of notches 169-1 and 169-2 and a distal pair of notches 171-1 and 171-2, notches 169-1 and 169-2 being disposed on opposite sides of slot 167 near the proximal end thereof, notches 171-1 and 171-2 being disposed on opposite sides of slot 167 near the distal end thereof. As will be described further below, proximal notches 169-1 and 169-2 and distal notches 171-1 and 171-2 are alternately adapted to receive, in a releasably locking fashion, a pair of pawls formed on button slide 121, notches 169-1 and 169-2 being adapted to receive said pawls in such a manner as to retain button slide 121 at a proximal position (as in FIGS. 3, 4 and 6(a)), notches 171-1 and 171-2 being adapted to receive said pawls in such a manner as to retain button slide 121 at a distal position (as in FIG. 6(b)).

A first pair of recesses 175-1 and 175-2 are formed on the inside surface of side portion 163-1, and a second pair of recesses 177-1 and 177-2 are formed on the inside surface of side portion 163-2. Recesses 175-1 and 175-2 are adapted to securely receive detents 143-1 and 143-2, respectively, of rail 141-1, and recesses 177-1 and 177-2 are adapted to securely receive detents 145-1 and 145-2, respectively, of rail 141-2. In this manner, body 117 and cover 119 may be secured to one another to form a handle. With body 117 and cover 119 thus coupled together, proximal end portion 165 of cover 119 is situated within the open proximal end of body 117, the open distal end of cover 119 terminates just proximally of post 149, and top portion 161 of cover 119 is spaced, for reasons to become apparent below, from the top surfaces of rails 141-1 and 141-2.

Referring now to FIGS. 9(a) through 9(e), button slide 121 is a unitary, generally rectangular member, preferably made of a durable molded plastic or other similarly suitable material, comprising an outer frame portion 181 and an inner tab portion 183. Frame portion 181, which is generally planar, is shaped to include a proximal end 185, a distal end 187, and a pair of sides 189-1 and 189-2, all of which collectively define an interior cavity 190. For reasons to become apparent below, frame portion 181 is appropriately dimensioned so that sides 189-1 and 189-2 are adapted to ride along the top surfaces of rails 141-1 and 141-2, respectively, and below a pair of ribs 188-1 and 188-2, respectively, formed on cover 119 (see FIGS. 8(c) through 8(e)).

Proximal end 185 of frame 181 is shaped to include a downwardly extending central portion 191, central portion 191 being dimensioned to extend downwardly a short distance through slot 142 of body 117. A slot 193 is provided in central portion 191, slot 193 extending upwardly a short distance from the bottom surface of portion 191. Slot 193 is shaped to include a pair of substantially orthogonal arms 193-1 and 193-2, which, as will be described further below, are adapted to matingly receive the proximal end of wire 105.

Distal end 187 is shaped to include a generally rectangular central portion 195, central portion 195 being dimensioned to extend downwardly a short distance through slot 142. A bore 197 is provided in central portion 195, bore 197 being aligned with arm 193-1 of slot 193 to receive an intermediate length of wire 105.

Inner tab portion 183 is generally trapezoidal in shape and includes a proximal end 201, a distal end 203 and a pair of sides 205-1 and 205-2. Proximal end 201 is hingedly connected to proximal end 185 of frame 181, with distal end 203 being free and upwardly biased. A pair of pawls 207-1 and 207-2 extend upwardly from sides 205-1 and 205-2, respectively, of tab portion 183. Pawls 207-1 and 207-2 are adapted to be received either within proximal notches 169-1 and 169-2, respectively, or distal notches 171-1 and 171-2, respectively, of cover 119.

A button 209 is provided on the top surface of tab portion 183 proximate to distal end 203, button 209 being adapted to extend upwardly through slot 167 of cover 119. With button 209 thus accessible through slot 167, an operator may use button 209 to exert downward pressure on tab portion 183 to disengage pawls 207-1 and 207-2 from either notches 169-1 and 169-2 or notches 171-1 and 171-2, as well as to slide button slide 121 proximally or distally along rails 141-1 and 141-2. Gripping elements 211 extend outwardly from the top of button 209 to facilitate manipulation of button 209.

Referring now to FIGS. 10(a) through 10(e), syringe connector 123 is a generally teardrop-shaped unitary member, preferably made of a durable molded plastic or another similarly suitable material, comprising a proximal end 221, a distal end 223 and a side 225. A port 227 extends proximally a short distance from proximal end 221, port 227 defining a tapered cavity 229 adapted to receive the medical luer of a syringe. The proximal end of port 227 is shaped to include a pair of radially outwardly extending tabs 229-1 and 229-2, tabs 229-1 and 229-2 being adapted for threaded engagement with the internally threaded sleeve of a syringe. Port 227 is oriented so that, with a syringe connected thereto and with connector 123 mounted on body 117, said syringe extends longitudinally through cavity 139 and on top of bottom portion 155 of body 117.

Figure 7A:
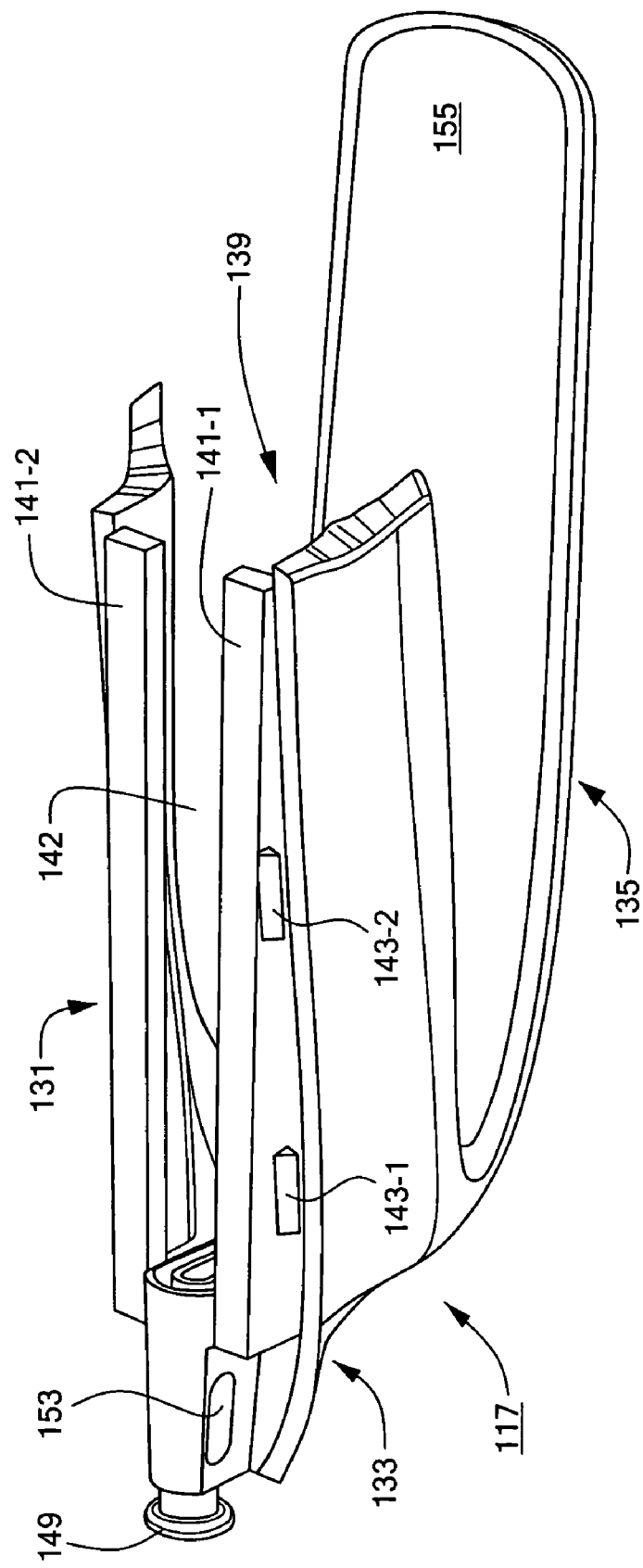
FIGS. 7(a) through 7(f) are perspective, side, top, proximal, distal and longitudinal section views, respectively, of the handle body shown in FIG. 3.
Figure 7B:
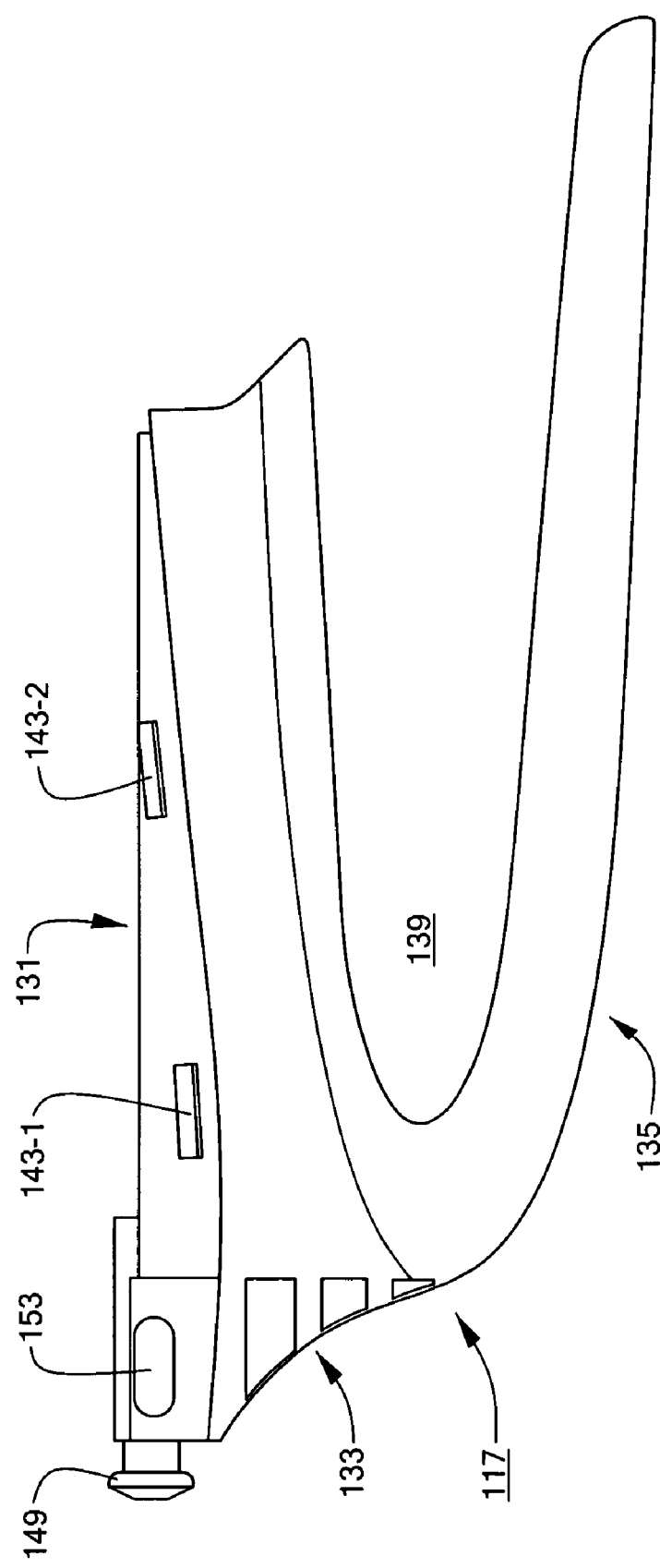
Figure 7C:
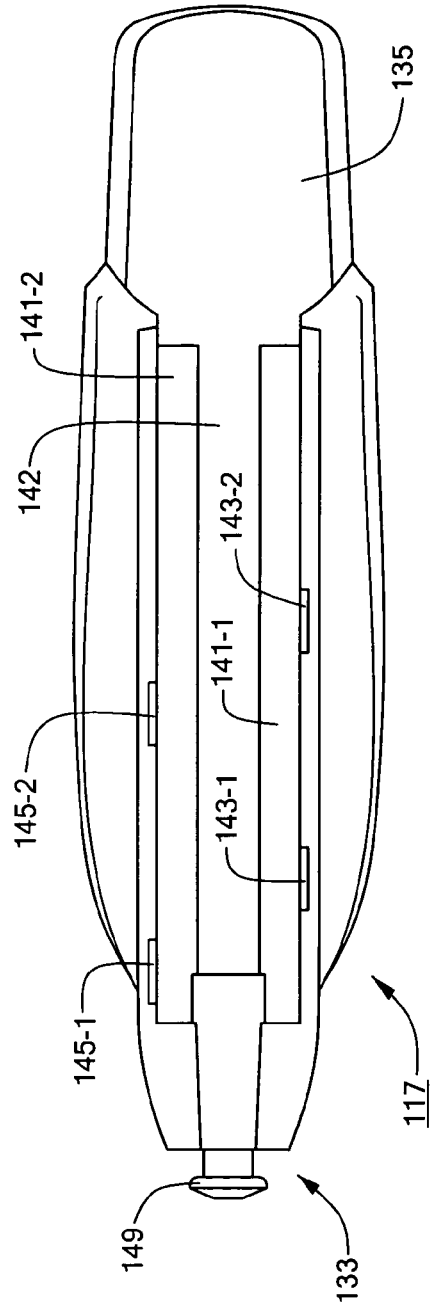
Figure 7E:
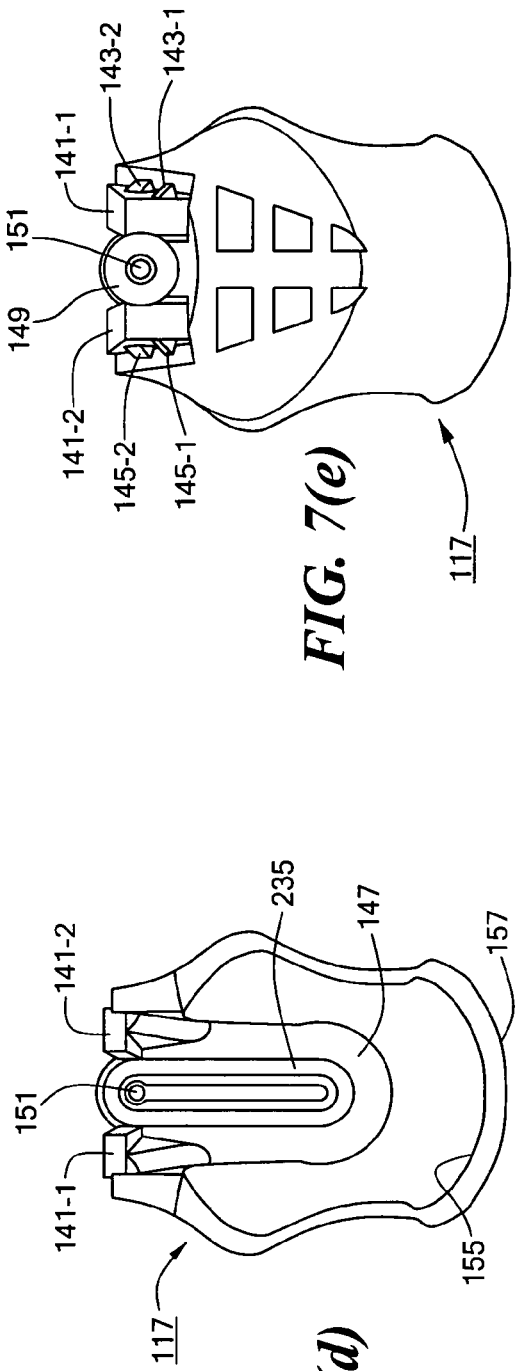
Figure 7D:
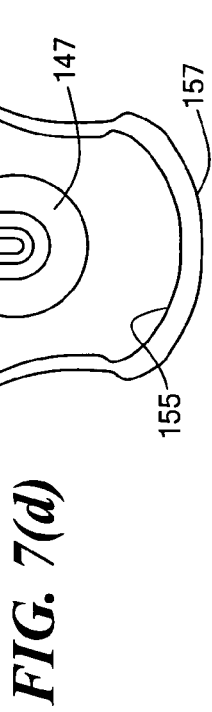
Figure 7F:
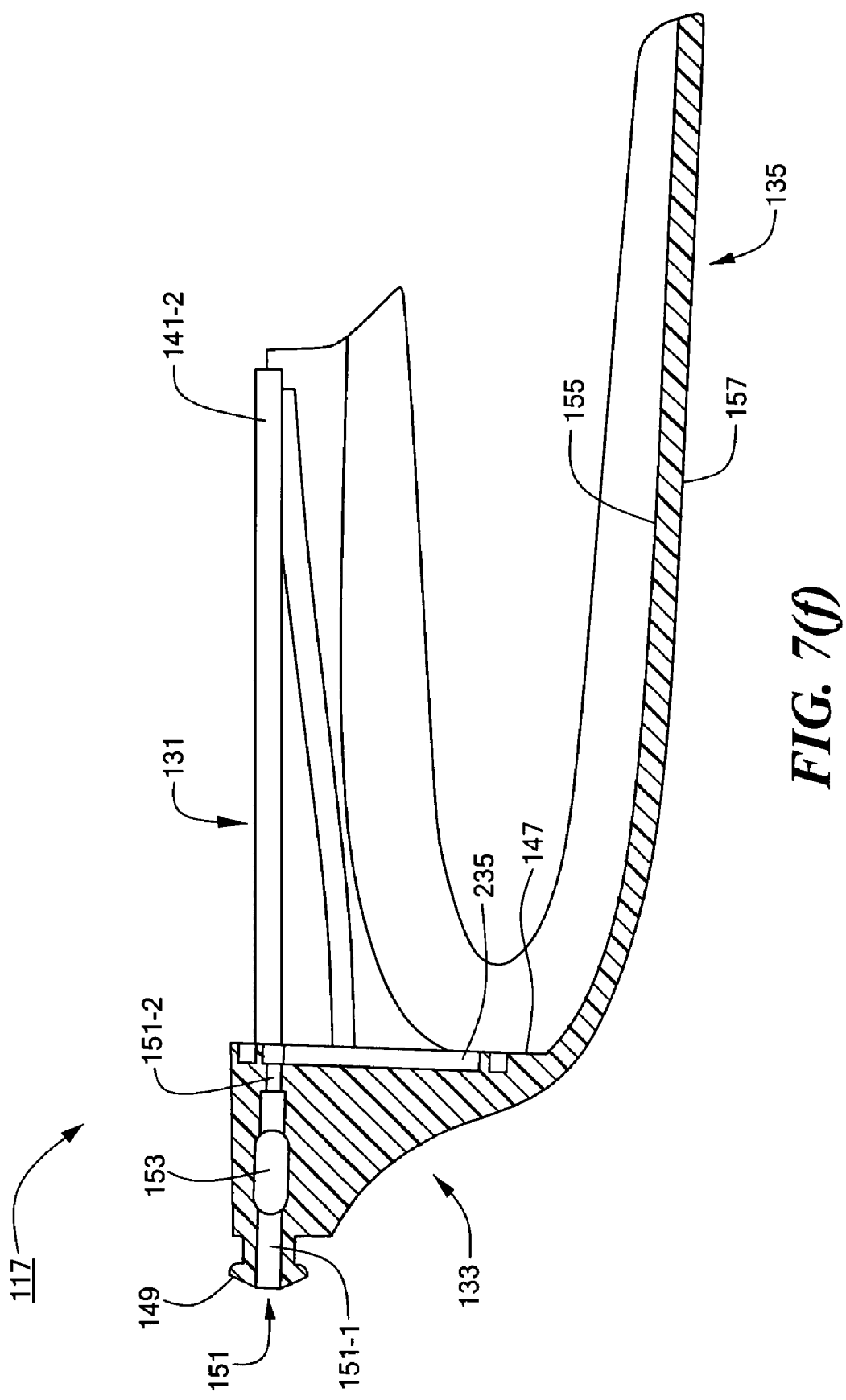
Figure 8A:
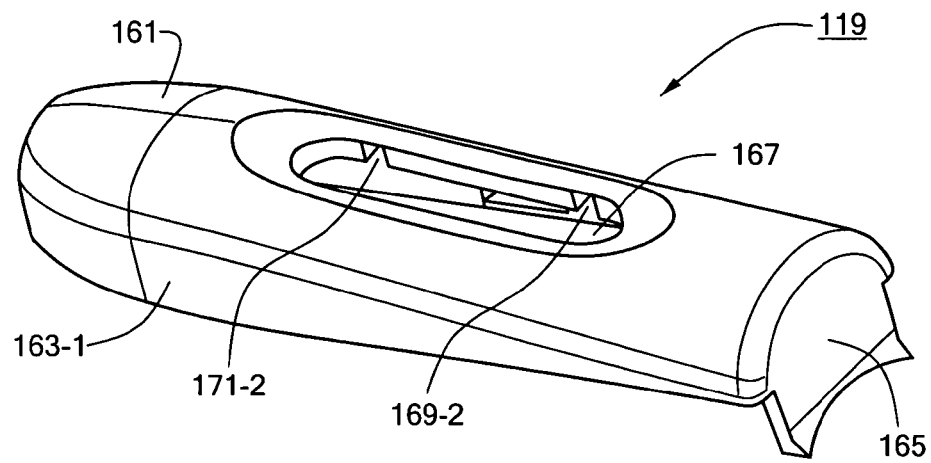
FIGS. 8(a) through 8(e) are perspective, top, bottom, left longitudinal section and right longitudinal section views, respectively, of the handle cover shown in FIG. 3.
Figure 8B:
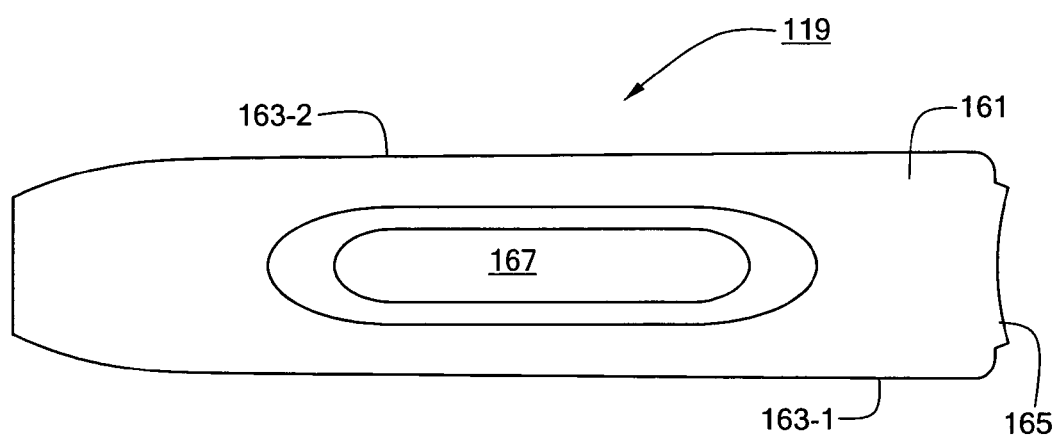
Figure 8C:
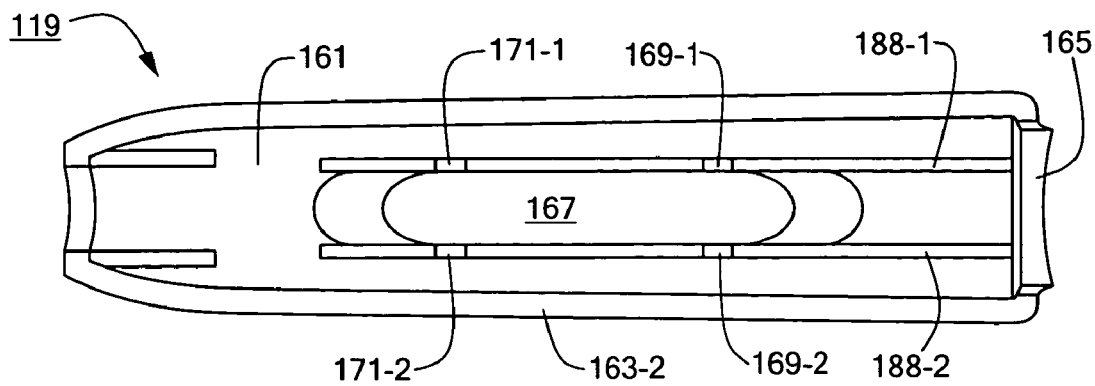
Figure 8D:
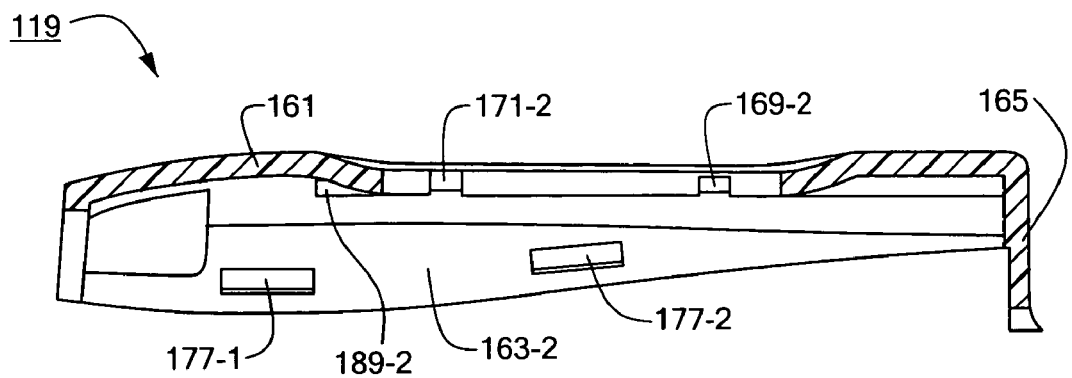
Figure 8E:
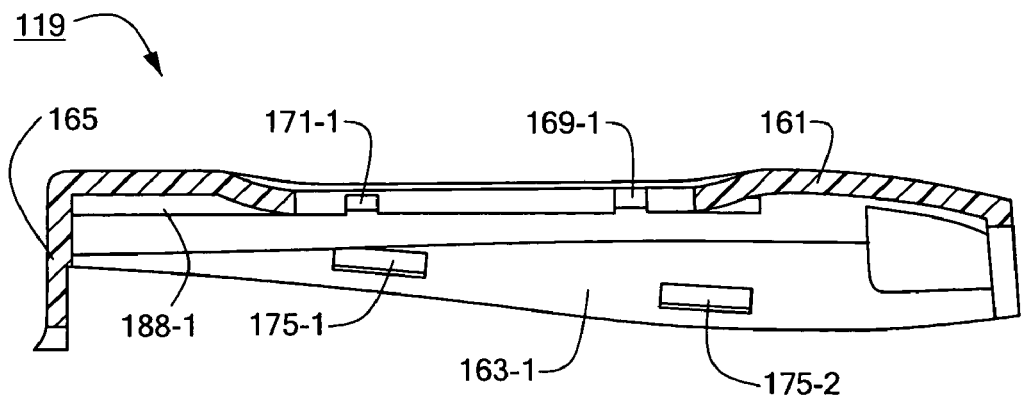
Figure 9A:
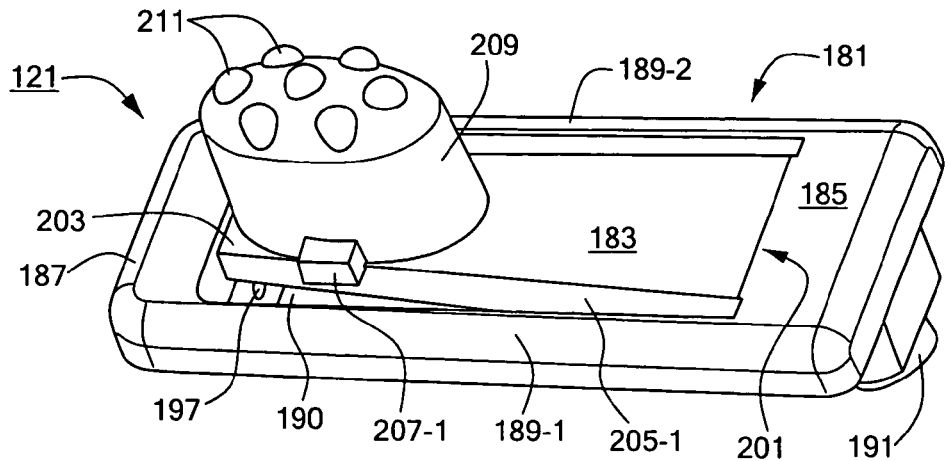
FIGS. 9(a) through 9(e) are perspective, top, bottom, right side and left longitudinal section views, respectively, of the button slide shown in FIG. 3.
Figure 9B:
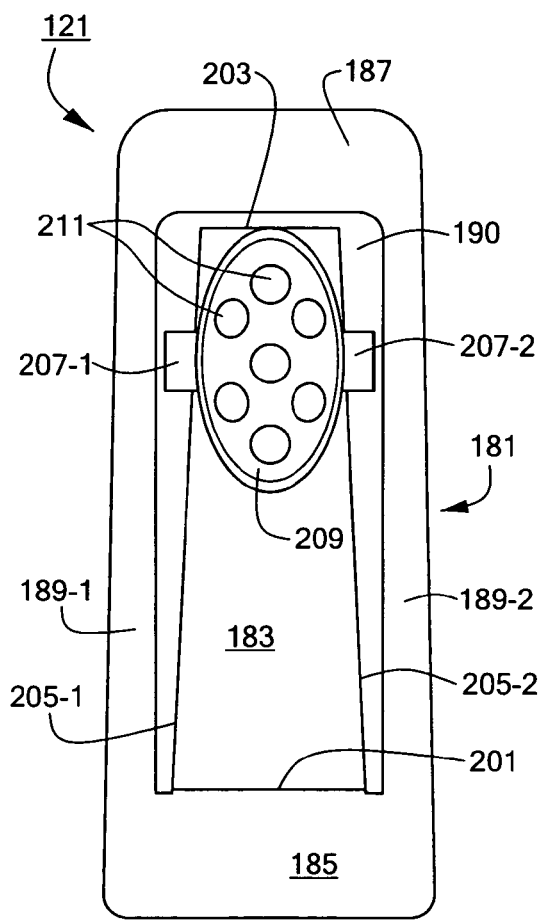
Figure 9C:
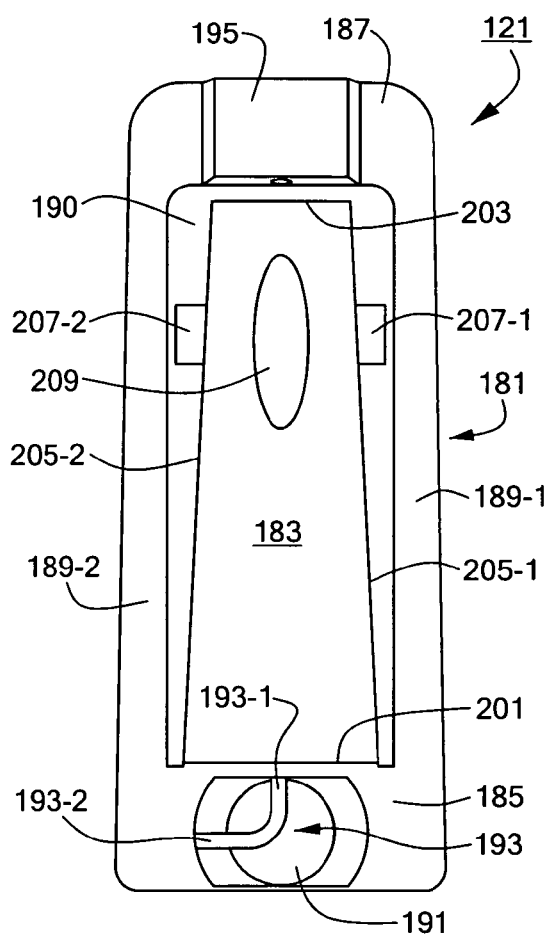
Figure 9D:
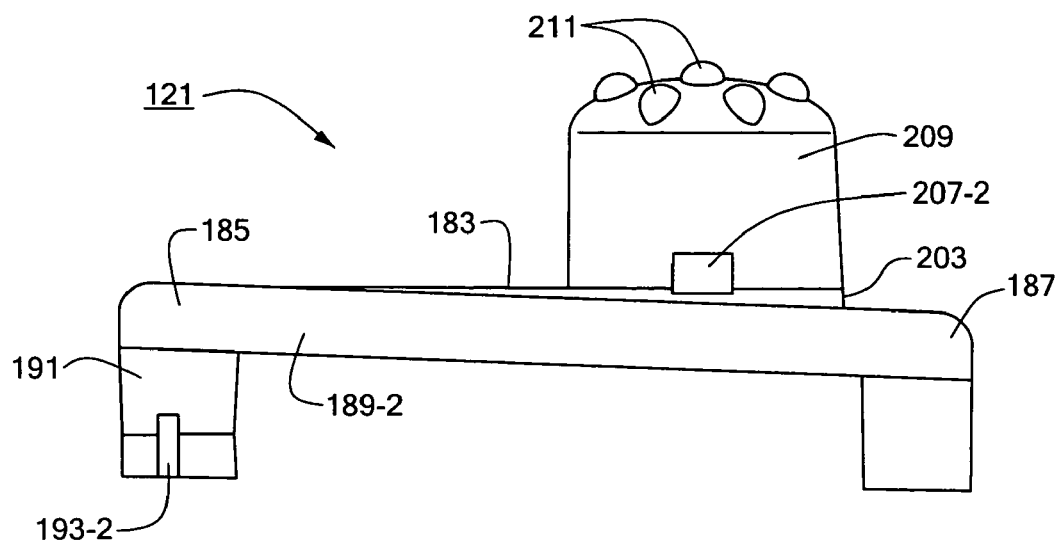
Figure 9E:
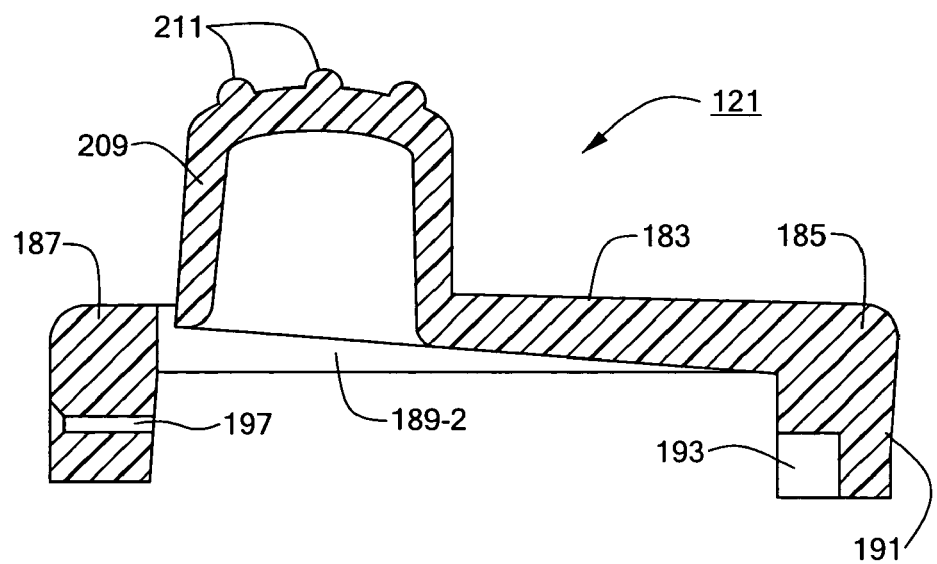
Figure 10A:
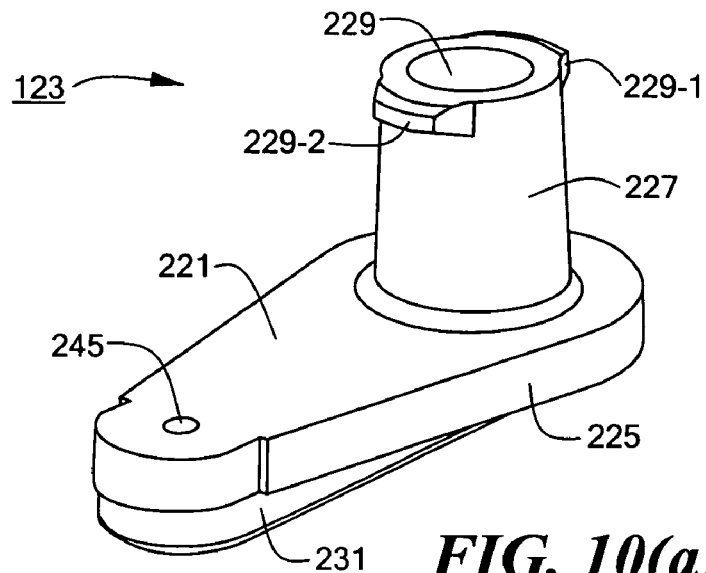
FIG. 10(a) through 10(e) are perspective, proximal, distal, right side and left longitudinal section views, respectively, of the syringe connector shown in FIG. 3.
Figure 10B:
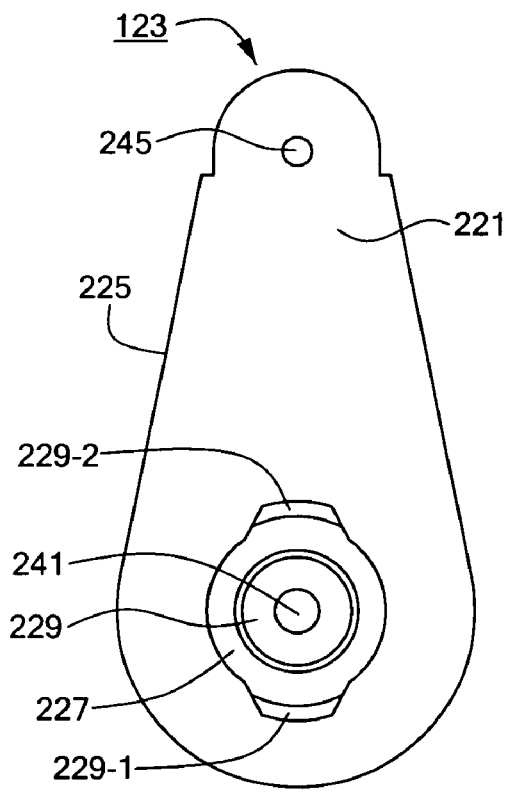
Figure 10C:
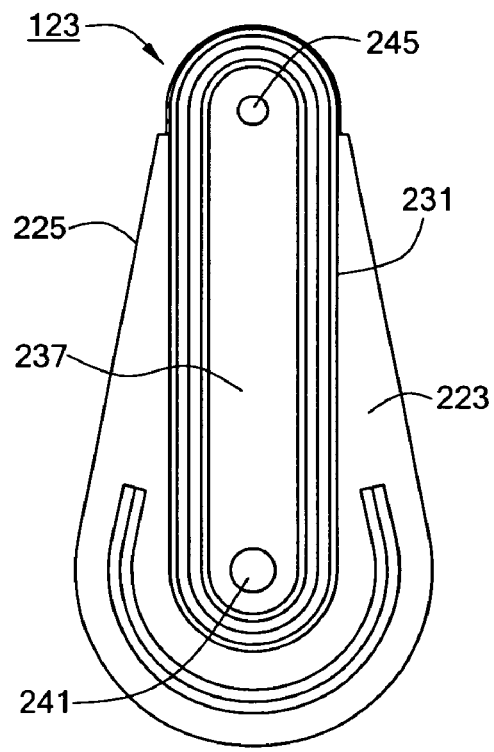
Figure 10D:
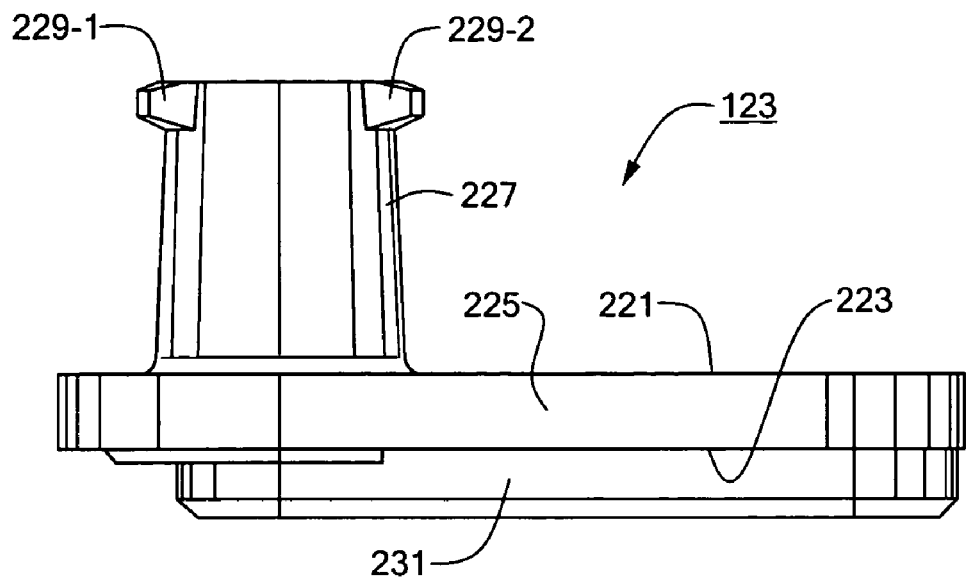
Figure 10E:
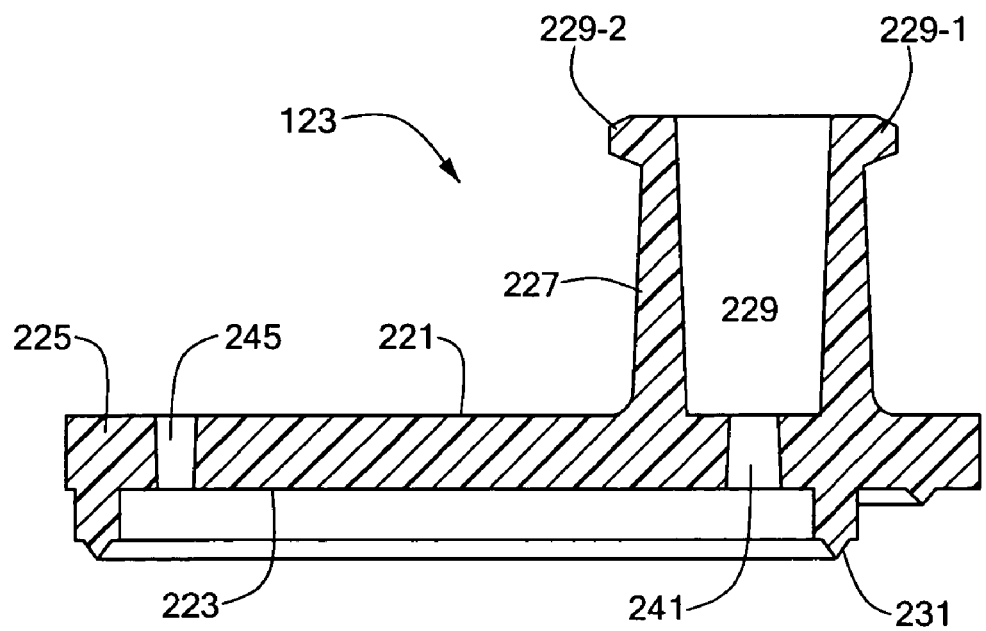
Figure 11B:
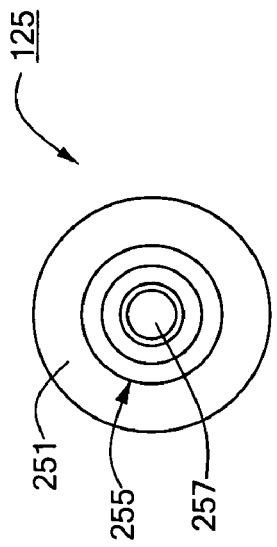
FIGS. 11(a) through 11(d) are perspective, proximal, right side and right longitudinal section views, respectively, of the strain relief member shown in FIG. 3.
Figure 11D:
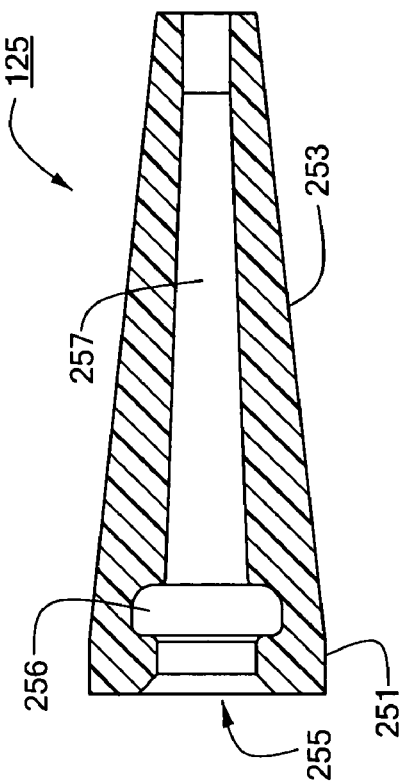
Figure 11A:
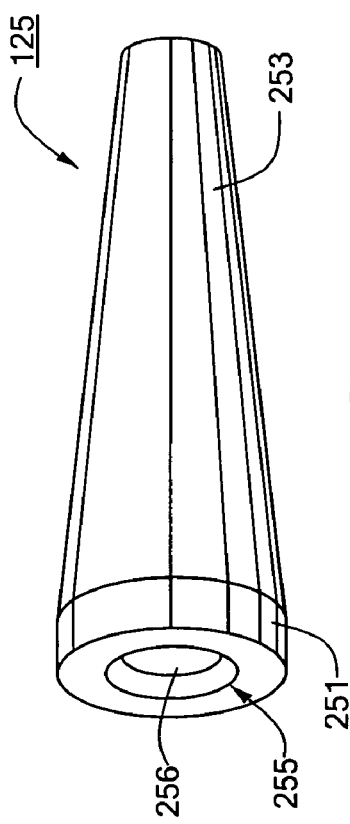
Figure 11C:
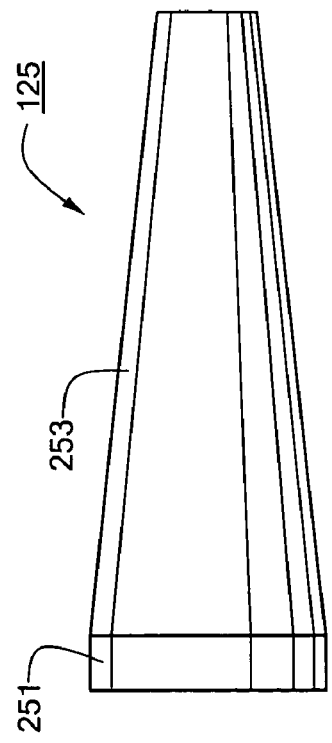

An oval-shaped ridge 231 extends distally a short distance from distal end 223, ridge 231 being receivable within a correspondingly shaped groove 235 provided in distal end portion 133 of body 117 (see FIG. 7(d)). An adhesive (not shown) may be used, if desired, to more securely retain ridge 231 within groove 235. Ridge 231 defines an oval-shaped cavity 237 that is adapted to bounded proximally by distal end 223 of syringe connector 123 and distally by distal end portion 133 of body 117. Cavity 237 is adapted to be aligned with distal portion 151-1 of bore 151 of body 117 for reasons to become apparent below.

A first transverse bore 241 extending between proximal end 221 and distal end 223 is provided in syringe connector 123, bore 241 being in fluid communication with each of cavity 229 and cavity 237. Accordingly, by connecting a syringe to connector 121, one can apply negative or positive suction force through cavity 229, bore 241, and cavity 237 and into bore 151.

A second transverse bore 245 extending between proximal end 221 and distal end 223 is provided in syringe connector 123, bore 245 being alignable with bore 151 for an intermediate portion of wire 105 to pass therethrough.

Referring now to FIGS. 11(a) through 11(d), strain relief member 125 is a unitary member, preferably made of a durable molded plastic or another similarly suitable material, comprising a generally cylindrical proximal portion 251 and a frustoconical distal portion 253. A longitudinal bore 255 extends the length of member 125, the proximal portion 256 of bore 255 being shaped to receive, among other things, post 149 of body 117, the distal portion 257 of bore 255 being shaped to receive, and thereby provide strain relief to, a length of catheter 107 proximate to the proximal end of catheter 107.

Figure 12B:
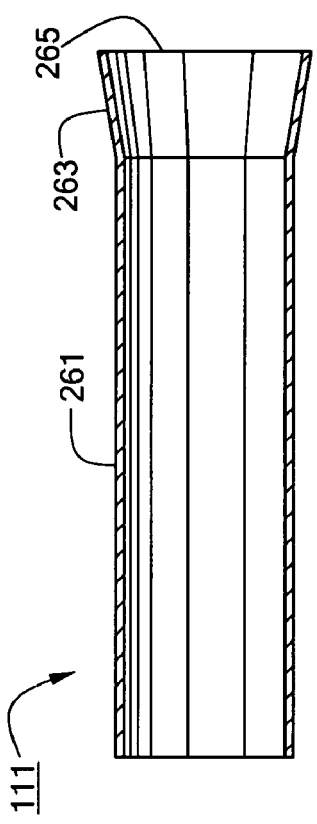
FIGS. 12(a) and 12(b) are perspective and right longitudinal section views, respectively, of the hub shown in FIG. 3.
Figure 12A:
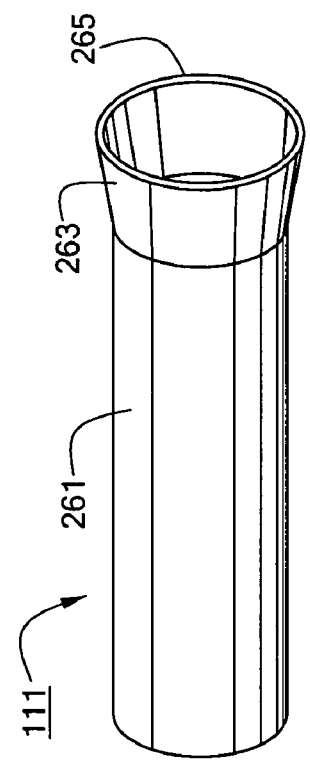

Referring now to FIGS. 12(a) and 12(b), hub 111 is a unitary tubular member, preferably made of stainless steel or another similarly suitable material, comprising a proximal portion 261 and a distal portion 263. Proximal portion 261 is straight and has a uniform diameter over its entire length. Distal portion 263 flares outwardly from proximal portion 261 to a distal end 265 for reasons to become apparent below. (It should be understood that the proximal end could also be outwardly flared, if desired.)

Referring back to FIGS. 3, 4, 5, 6(a) and 6(b), catheter 107 is a unitary flexible tubular member, preferably made of nylon or another similarly suitable material, having a length of about 160 cm and comprising a proximal end 271 and a distal end 273. Proximal end 271 of catheter 107 is coaxially received and fixedly secured within distal portion 151-1 of bore 151. As seen best in FIGS. 6(a) and 6(b), catheter 107 is dimensioned relative to hub 111 so that hub 111 may be press-fit into catheter 107 through distal end 273, with distal end 273 of catheter 107 being inverted over distal end 265 of hub 111 and shaped to define an opening 275. Although not shown herein, the shaping of distal end 273 of catheter 107 around distal end 265 of hub 111 to define opening 275 may be performed by inserting a mandrel through hub 111 and catheter 107 and then using heat to shape distal end 273 to said mandrel. Preferably, opening 275 of catheter 107 is dimensioned to conform closely to the outer diameter of a shaft 277 of needle 109 to promote an air-tight seal between shaft 277 and catheter 107 when needle 109 is extended through opening 275 (as in FIG. 6(b)). Alternatively, one could position an annular seal (not shown) coaxially within catheter 107 between distal end 273 of catheter 107 and distal end 265 of hub 111, said annular seal being appropriately dimensioned and made of a suitable material to promote an air-tight interface with the outer surface of needle 109 inserted therethrough.

Figure 13:
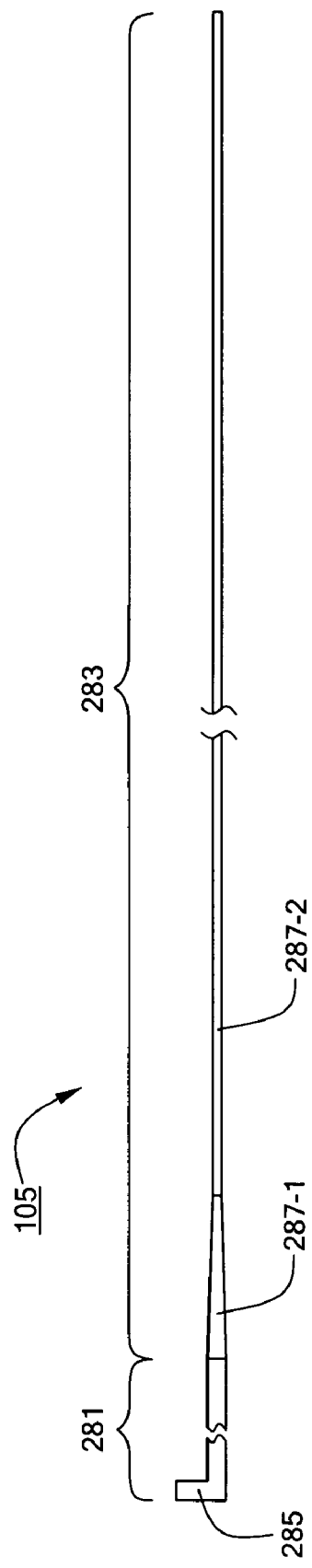
FIG. 13 is a fragmentary right side view of the wire shown in FIG. 3.

Referring now to FIG. 13, wire 105 is a solid flexible unitary member, preferably made of stainless steel or another similarly suitable material, comprising a proximal portion 281 and a distal portion 283. Proximal portion 281, which has a length of about 52 inches and a thickness of about 0.022 inch, includes a proximal end 285. Proximal end 285 is bent into an L-shape and is adapted to be securely received within slot 193 of button slide 121. The remainder of proximal portion 281 is adapted to be inserted through bore 197 of button slide 121, through an annular seal 291 (see FIGS. 4 and 5) positioned between button slide 121 and syringe connector 123, through bore 245 of syringe connector 123, through bore 151 of body 103 and into catheter 107, terminating a few inches proximally of hub 111.

Distal portion 283, which has a length of about 2 inches, is shaped to include a proximal segment 287-1 and a distal segment 287-2. Proximal segment 287-1 has a length of about 0.2 inch and decreases uniformly in thickness from about 0.022 inch at its proximal end to about 0.01 inch at its distal end. Distal segment 287-2, which extends distally from segment 287-1, has a length of about 1.8 inch and a uniform thickness of about 0.01 inch over its entire length.

As will be described further below, the reason for providing a reduced thickness over much of the length of distal portion 283 of wire 105 is to endow distal portion 283 with additional flexibility, which may be advantageous in enabling distal portion 283 to be delivered to certain remote sampling sites accessible only through contorted paths. Endowing distal portion 283 of wire 105 with additional flexibility may also be advantageous in allowing passage through aggressive scope channels. Notwithstanding the above, distal portion 283 may be varied in size and/or shape depending upon the characteristics desired therefor.

Referring now to FIGS. 14(a) and 14(b), jacket 113 is a unitary tubular member, preferably made of arnitel, polypropylene or another similarly suitable material. Jacket 113 is shaped to include a proximal end 301, a distal end 303, a central bore 305, and a plurality of external ribs 307-1 through 307-4. Bore 305 is appropriately dimensioned to securely receive wire 105 by a friction-fit, with proximal end 301 of jacket 113 being aligned with that portion of wire 105 that is disposed within distal portion 151-1 of bore 151 when button slide 121 is in its retracted position and with distal end 303 of jacket 113 being aligned with that portion of wire 105 that is positioned just proximally of distal portion 283. An alternative to the aforementioned friction-fit between wire 105 and jacket 113 is a sliding-fit between wire 105 and jacket 113. Such a sliding-fit allows wire 105 to move with respect to jacket 113 in situations where jacket 113 encounters resistance when sliding within catheter 107. This allows for movement of wire 105 to occur in the manner of least resistance.

Ribs 307-1 through 307-4, which extend longitudinally along the entire length of jacket 113, are evenly spaced about the circumference of jacket 113. Each of ribs 307-1 through 307-4 extends in a direction radially outwardly from bore 305 and is generally triangular in shape, as viewed from an end of jacket 113. Ribs 307-1 through 307-4 are appropriately sized so that at least one of their respective vertices 309-1 through 309-4 is adapted to be in contact with the inside surface of catheter 107. In this manner, ribs 307-1 through 307-4 serve to keep wire 105 substantially centered within catheter 107 throughout its length (even when a load force is applied to needle 109) while, at the same time, providing ample space (i.e., between adjacent ribs 307) for fluid flow within catheter 107.

As can readily be appreciated, there are a myriad number of ways in which ribs 307-1 through 307-4 may be changed in size, shape and number while still satisfying the foregoing objectives of keeping wire 105 centered within catheter 107 and providing an ample volume within catheter 107 for fluid flow. (For examples of these and other modifications, see commonly-assigned U.S. Pat. No. 6,454,702 and commonly-assigned U.S. patent application Ser. No. 09/716,710, both of which are incorporated herein by reference.)

In another embodiment (not shown), one could replace jacket 113 with a plurality of beads or similarly suitable elements over-molded around wire 105 at spaced intervals thereof, said beads being sized to engage the inside surface of catheter 107 and, thus, to keep wire 105 centered within catheter 107. If desired, said beads could have longitudinal grooves or channels oriented along the longitudinal axis of catheter 107 to allow maximum fluid flow from the proximal to the distal portions of catheter 107 and vice versa. The dimensions of said beads may also be chosen so as to regulate fluid flow by controlling the gap between the bead surface and catheter 107.

In still another embodiment (not shown), one could replace both jacket 113 and wire 105 with a wire that is shaped (e.g., by machining, stamping, etc.) to include one or more elements adapted to keep said wire centered within catheter 107.

Figure 16A:
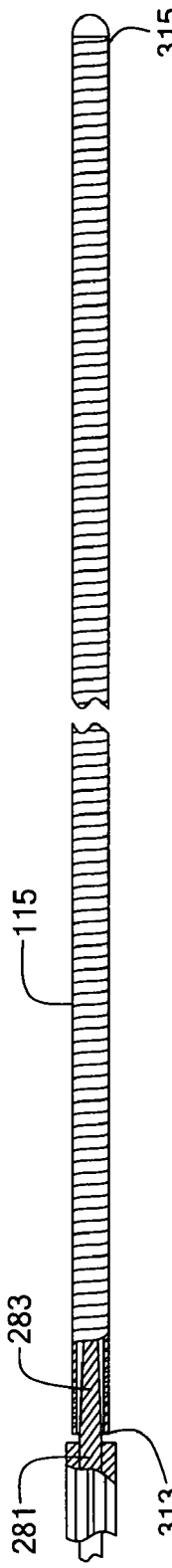
FIGS. 16(a) through 16(c) are fragmentary right side, fragmentary right longitudinal section and fragmentary enlarged right longitudinal section views, respectively, of the combination of the wire, the jacket and the spring shown in FIG. 3.
Figure 16B:
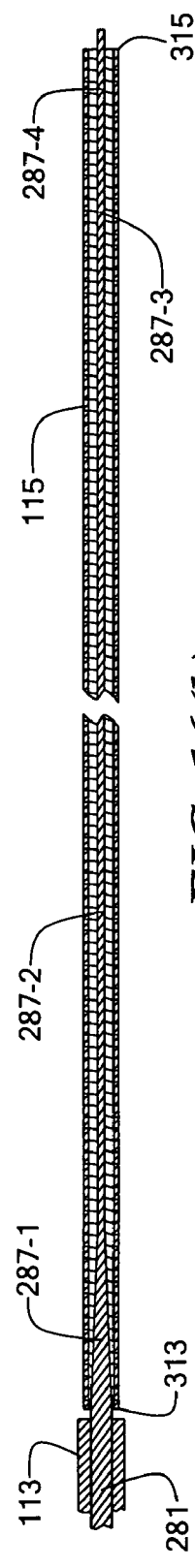
Figure 16D:
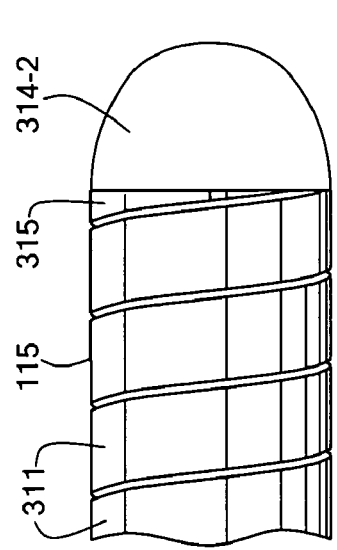
FIG. 16(d) is an enlarged right side view showing the distal ends of the spring and the wire shown in FIG. 16(a)
Figure 16C:
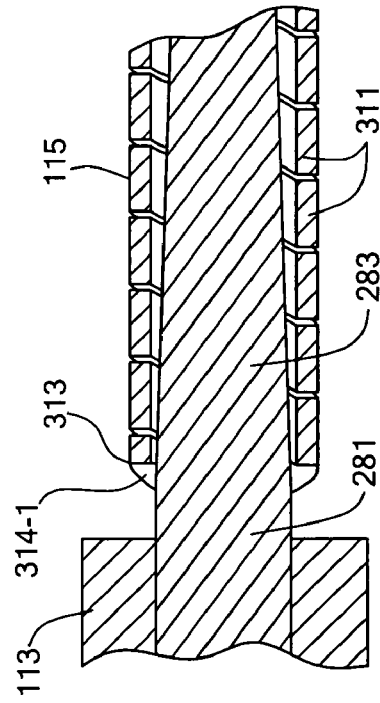
Figure 17C:
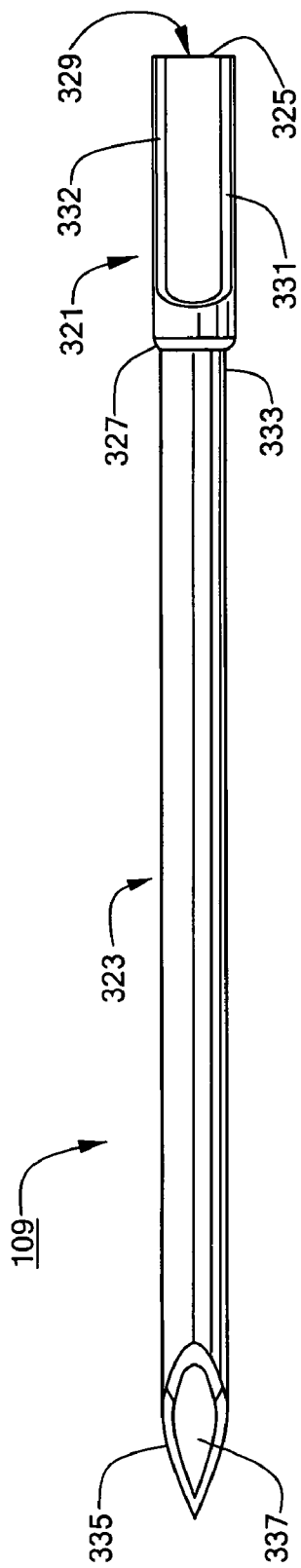
Figure 17D:
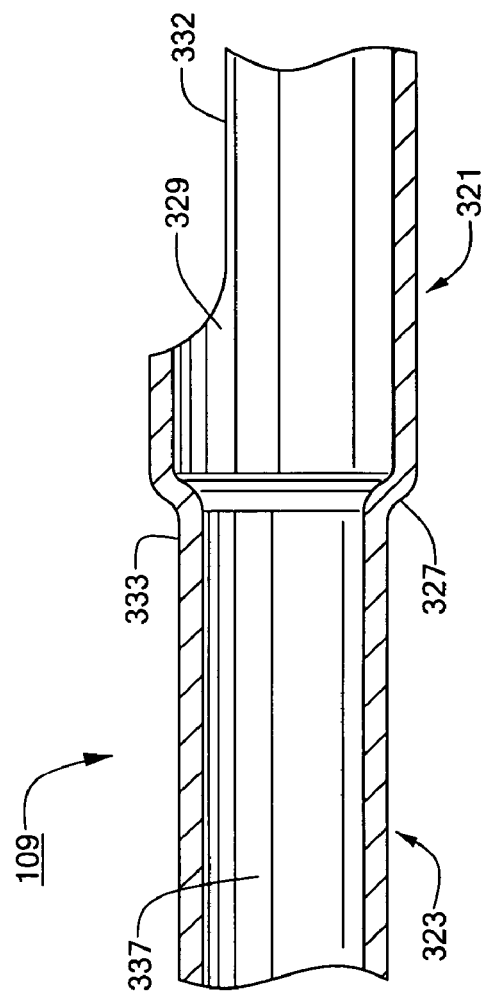

Referring now to FIGS. 15(a) and 15(b), spring 115 is a unitary member, preferably made of stainless steel or another similarly suitable material, comprising a plurality of closely spaced or compressed coils 311 terminating at a proximal end 313 and a distal end 315. (Although coils 311 are shown in the present embodiment having a rectangular transverse cross-sectional shape, it is to be understood that coils 311 are not limited to a rectangular transverse cross-sectional shape and could have, for example, a circular transverse cross-sectional shape or the like.) As seen best in FIGS. 16(a) through 16(c), spring 115 coaxially surrounds distal portion 283 of wire 105, with proximal end 313 of spring 115 being secured, preferably by a weld 314-1 (see FIG. 16(c)) or like means, to wire 105 just proximally of segment 287-1 and with distal end 315 of spring 115 being secured, preferably by a weld 314-2 (see FIG. 16(d)) or like means, to the distal end of segment 287-2. Spring 115 has a uniform inner diameter of about 0.026 inch, which is slightly greater than the thickness of wire 105, and a uniform outer diameter of about 0.034 inch.

The purpose of spring 115 is to provide greater column strength to distal portion 283 of wire 105, i.e., to make distal portion 283 less likely to buckle when a compressive force is applied thereto. Such increased column strength is desirable since, as noted above, distal portion 283 has a decreased thickness as compared to the remainder of wire 105. One advantageous feature of spring 115 is that, whereas spring 115 cannot be compressed and, therefore, provides the aforementioned column strength to distal portion 283, spring 115 can be bent and, therefore, does not substantially diminish the flexibility of distal portion 283.

Referring now to FIGS. 17(a) through 17(d), needle 109 is a unitary member, preferably made of stainless steel or another similarly suitable material, comprising a proximal base portion 321 and a distal stem portion 323. Base portion 321, which is generally cylindrical in shape, is about 0.2 inch in length and includes a proximal end 325, a rounded distal end 327, a longitudinal bore 329 and an upwardly-facing slot 331, slot 331 extending distally from proximal end 325 to a point just prior to distal end 327. Slot 331 is bounded by a flat edge 332 onto which wire 105 may be secured, preferably by welding or like means.

Stem portion 323, which is generally cylindrical in shape and coaxial with base portion 321, is about 0.8 inch in length and includes a proximal end 333, a distal end 335 and a longitudinal bore 337. Distal end 335 is shaped to define an upwardly-facing, open-ended tip, said tip being appropriately shaped and dimensioned to acquire a tissue sample for biopsy. As in the embodiment shown, slot 331 and the tip of needle 109 both face in the same direction; in this manner, wire 105 may be (but is not necessarily) welded to needle 109 on the same side as the tip. This permits force applied to the tip to be transmitted along the axis of wire 105. When joining wire 105 to needle 109, a small space is left between the distal end of wire 105 and the distal end of slot 331, said space being appropriately sized to permit fluid flow between catheter 107 and longitudinal bores 337 and 329 of needle 109 while, at the same time, preventing passage of the sample from needle 109 into catheter 107. This gap may be varied in size and/or length to regulate fluid flow for a given purpose.

Rounded distal end 327 of base portion 321 and proximal end 333 of stem portion 323 together define a shoulder that is shaped to abut directly the proximal end of hub 111 in such a way as to form an air-tight seal therewith when needle 109 is placed in its advanced position.

As discussed above, the outer diameter of stem portion 323 is appropriately dimensioned to form a tight seal with distal end 273 of catheter 107 when needle 109 is moved to its extended position (see FIG. 6(b)). In addition, as noted above, the shoulder formed by rounded distal end 327 of base portion 321 and proximal end 333 of stem portion 323 is appropriately dimensioned to engage proximal end 261 of hub 111 so as to form a seal therewith, as well as to delimit distal movement of needle 109 (and, in so doing, prevent needle 109 from being lost distally from the remainder of device 101 and, perhaps, becoming lost in a patient). Although not shown, one could, if desired, enhance the seal formed between the shoulder of needle 109 and proximal end 261 of hub 111 by heat-shrinking an elastomeric sleeve over the shoulder of needle 109, said sleeve conforming to the shape of the shoulder and forming a sealing interface with the proximal end 261 of hub 111. (It should be noted that the use of such an elastomeric sleeve in device 101 would make considerably more difficult any reprocessing of device 101.)

Figure 18A:
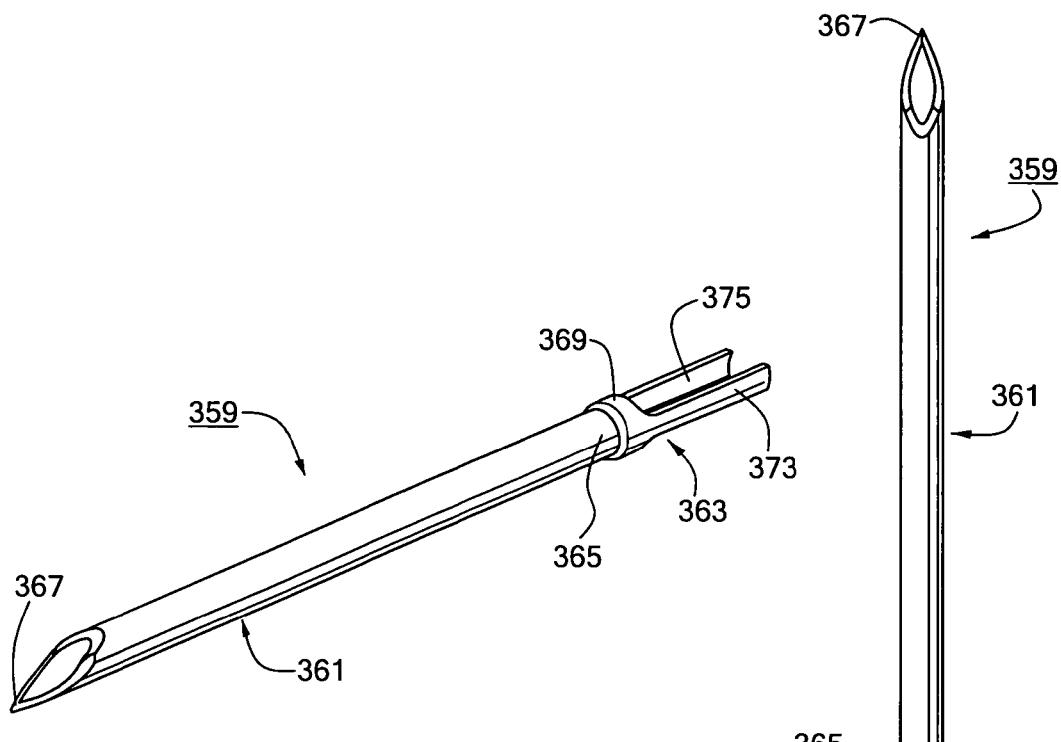
FIGS. 18(a) through 18(c) are perspective, top and left side views, respectively, of a first alternate needle.
Figure 18B:
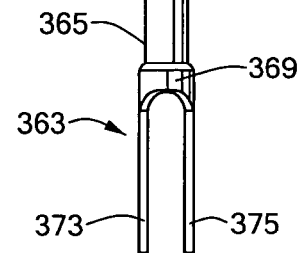
Figure 18C:
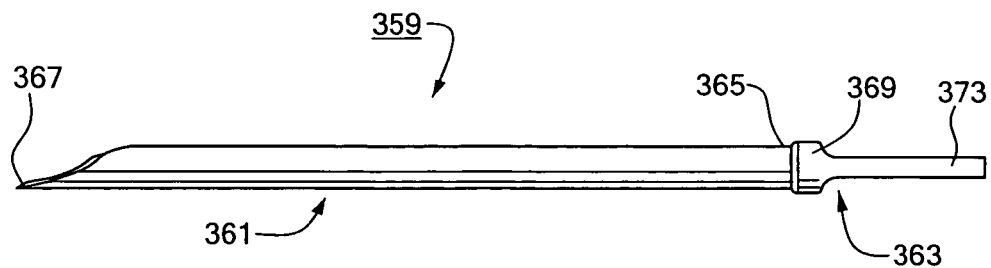

Referring now to FIGS. 18(a) through 18(c), there are shown various views of a first alternate needle usable instead of needle 109 in device 101, said first alternate needle being constructed according to the teachings of the present invention and being represented generally by reference numeral 359.

Needle 359 is a unitary structure shaped to include a stem portion 361 and a base portion 363. Stem portion 361, which is substantially identical to stem portion 323 of needle 109, is a generally tubular element shaped to include a proximal end 365 and a distal end 367, distal end 367 being an upwardly-facing, open-ended tip.

Base portion 361 includes a distal portion 369 and a proximal portion. Distal portion 369, which is generally tubular in shape, forms a shoulder with proximal end 365 of stem portion 361. The proximal portion of base portion 361 is bifurcated into a left side member 373 and a right side member 375, left side member 373 and right side member 375 being centered relative to the top and bottom surfaces of distal portion 369 of base portion 361. Wire 105 may be mounted along the top or bottom surfaces of left and right side members 373 and 375, respectively.

Referring now to FIGS. 19(a) through 19(c), there are shown various views of a second alternate needle usable instead of needle 109 in device 101, said second alternate needle being constructed according to the teachings of the present invention and being represented generally by reference numeral 379.

Needle 379 is a unitary structure shaped to include a stem portion 381 and a base portion 383. Stem portion 381, which is substantially identical to stem portion 323 of needle 109, is a generally tubular element shaped to include a proximal end 385 and a distal end 387, distal end 387 being an upwardly-facing, open-ended tip.

Base portion 383 is a generally tubular element shaped to include a transverse slot 389 extending distally a short distance from the proximal end of base portion 383. Slot 389, which is appropriately sized for wire 105 to be mounted therewithin, extends from the left side of base portion 383 to the right side of base portion 383 and is centered relative to the top and bottom surfaces of base portion 383.

One desirable attribute of needle 379 is that slot 389 permits wire 105 to be coupled to needle 379 in such a way that wire 105 and needle 379 share a common axis.

In use, prior to inserting device 101 into a bronchoscope, an operator typically tests device 101 by using button slide 121 to alternately position needle 109 in its advanced position and its retracted position. Once the operability of said needle positioning mechanism has been confirmed, needle 109 is then locked in its retracted position by positioning slide 121 so that pawls 207-1 and 207-2 are positioned within notches 169-1 and 169-2, respectively. The distal end of device 101 is then loaded into a bronchoscope (which has previously been inserted into the patient to a neutral location), and a syringe is attached to port 227 of connector 123. Once confirmation is received that distal end 273 of device 101 has passed entirely through the bronchoscope (such confirmation typically being provided using a video channel of the same bronchoscope), the bronchoscope and device 101 are advanced together to the target site, and needle 109 is advanced to its extended position by positioning slide 121 so that pawls 207-1 and 207-2 are positioned within notches 171-1 and 171-2, respectively. Distal end 335 of needle 109 is then inserted through the bronchial wall of the patient and into a nearby lymph node. At this time, the syringe is used to apply suction. In the unfortunate event that needle 109 has errantly penetrated a blood vessel, instead of a lymph node, the application of suction causes blood to be aspirated through bore 337 of needle 109 and into catheter 107 and the syringe, where such blood is detected. In such a case, the application of suction is discontinued and the soiled device 101 is removed from the bronchoscope and the patient. A fresh TBNA device 101 is then loaded into the bronchoscope and the patient in the manner described above, and another attempt is made to penetrate the lymph node.

If, while suction is applied, it appears that needle 109 has penetrated a lymph node, as is desired, catheter 107 is agitated to help shear tissue from the penetrated lymph node into bore 337 of needle 109. With a tissue sample thus disposed within bore 337 of needle 109, needle 109 is moved back to its retracted position within catheter 107 by positioning slide 121 so that pawls 207-1 and 207-2 are positioned within notches 169-1 and 169-2, respectively. Device 101 is then removed from the bronchoscope and the patient. Needle 109 is then placed in its advanced position by positioning slide 121 so that pawls 207-1 and 207-2 are positioned within notches 171-1 and 171-2, respectively, and negative suction is then used to expel the tissue from needle 109 onto a slide or the like for histological examination.

Device 101 is intended to be a single-use device. However, it is envisioned that, if device 101 is constructed from materials capable of withstanding reprocessing conditions, e.g., flushing with suction, followed by (or preceded by) washing in an ultrasonic bath, flushing again with suction, and then autoclaving, device 101 may be reprocessed for additional use.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A tissue sampling device, said tissue sampling device comprising:
   (a) a flexible catheter, said flexible catheter having a proximal end and a distal end;
   (b) a sampling needle, said sampling needle being slidably disposed at said distal end of said flexible catheter and having a distal tip;
   (c) a wire, said wire being inserted into said flexible catheter and having a proximal end and a distal end, said distal end of said wire being fixed to said sampling needle; and
   (d) a handle assembly, said handle assembly comprising a handle and a button slide, said handle being ergonomic and specially constructed to fit into a hand of an operator, said handle being secured to said proximal end of said flexible catheter, said handle including a port, a bore, and a lumen, said port being oriented parallel to, but off-set from, said bore, said port being adapted to receive a syringe, said bore being aligned with and in fluid communication with said proximal end of said flexible catheter, said lumen fluidly interconnecting said port and said bore and being generally perpendicular to each of said port and said bore, said button slide being slidably mounted within said handle between a proximal position within said handle and a distal position within said handle and being fixed to said proximal end of said wire to cause said sampling needle to move relative to said flexible catheter, said button slide including a button accessible through the handle for manipulation by an operator.

2. The tissue sampling device as claimed in claim 1 further comprising a tubular hub, said tubular hub having a proximal end and a distal end, said tubular hub being coaxially mounted within said flexible catheter, with said distal end of said flexible catheter being sealed around said distal end of said tubular hub to secure said tubular hub within said flexible catheter, said distal end of said flexible catheter defining an opening.

3. The tissue sampling device as claimed in claim 2 wherein said distal end of said tubular hub is outwardly flared.

4. The tissue sampling device as claimed in claim 2 wherein said opening is sized to form a seal with said sampling needle when said sampling needle is extended through said opening.

5. The tissue sampling device as claimed in claim 1 further comprising a tubular hub, said tubular hub having a proximal end and a distal end, said tubular hub being coaxially mounted within said flexible catheter, with said distal end of said flexible catheter being inverted over said distal end of said tubular hub, said distal end of said flexible catheter defining an opening.

6. The tissue sampling device as claimed in claim 1 wherein said flexible catheter has an inner diameter and wherein said wire has an outer diameter, said outer diameter of said wire being less than said inner diameter of said flexible catheter.

7. The tissue sampling device as claimed in claim 6 further comprising means inserted over at least a portion of said wire for centering said wire within said flexible catheter while still providing a space for fluid flow.

8. The tissue sampling device as claimed in claim 7 wherein said centering means comprises a jacket inserted over at least a portion of said wire, said jacket having a plurality of longitudinal ribs adapted to contact the inner diameter of said flexible catheter.

9. The tissue sampling device as claimed in claim 8 wherein said jacket is sized to permit said wire to slide longitudinally relative to said jacket and to permit said jacket to slide longitudinally relative to said flexible catheter so that movement occurs at an interface of least friction.

10. The tissue sampling device as claimed in claim 1 wherein said handle comprises a proximal notch and a distal notch and wherein said button slide comprises a pawl, said pawl being alternately releasably lockably retained in said proximal notch and in said distal notch to alternately position said sampling needle in a retracted position wherein said distal tip of said sampling needle is disposed within said flexible catheter and in an extended position wherein said distal tip of said sampling needle extends distally beyond said distal end of said flexible catheter, respectively.

11. The tissue sampling device as claimed in claim 1 wherein said handle is shaped to include a slot and wherein said button slide comprises an outer frame portion and an inner tab portion, said outer frame portion comprising a proximal end, a distal end, a pair of sides, and an interior cavity, said inner tab portion comprising a proximal end and a distal end, said proximal end of said inner tab portion being hingedly connected to said proximal end of said outer frame portion, said distal end of said inner tab portion being free and biased towards said slot in said handle, wherein said button is provided on said inner tab portion proximate to said distal end, said button being adapted to extend through said slot.

12. The tissue sampling device as claimed in claim 11 wherein said handle further comprises a proximal notch and a distal notch and wherein said inner tab portion further comprises a pawl, said pawl being alternately releasably lockably retained in said proximal notch and in said distal notch to alternately position said sampling needle in a retracted position wherein said distal tip of said sampling needle is disposed within said flexible catheter and in an extended position wherein said distal tip of said sampling needle extends distally beyond said distal end of said flexible catheter, respectively.

13. A tissue sampling device, said tissue sampling device comprising:
   (a) a flexible catheter, said flexible catheter having a proximal end and a distal end;
   (b) a sampling needle, said sampling needle being slidably disposed at said distal end of said flexible catheter and having a distal tip;
   (c) a wire, said wire being inserted into said flexible catheter and having a proximal end and a distal end, said distal end of said wire being fixed to said sampling needle; and
   (d) a handle assembly, said handle assembly comprising a handle and a button slide, said handle being ergonomic and specially constructed to fit into a hand of an operator, said handle being secured to said proximal end of said flexible catheter, said handle comprising a body, a cover, and a syringe connector, said body comprising a generally C-shaped member comprising a top portion, a distal end portion, and a bottom portion, said top portion, said distal end portion, and said bottom portion collectively defining a cavity for receiving a syringe, said distal end portion of said body comprising a bore aligned with and in fluid communication with said flexible catheter, said cover being mounted on said top portion of said body, said cover comprising a slot, said syringe connector being mounted on a proximal surface of said distal end of said body and comprising a port adapted for connection to a syringe, said port being oriented parallel to, but off-set from, said bore, said body and said syringe connector jointly defining a lumen, said lumen fluidly interconnecting said port and said bore and being generally perpendicular to each of said port and said bore, said button slide being slidably mounted in said handle and being fixed to said proximal end of said wire to cause said sampling needle to move relative to said flexible catheter, said button slide including a button extending through said slot in said cover for manipulation by an operator.

14. The tissue sampling device as claimed in 13 wherein said bottom portion of said body has a top surface and a bottom surface, said top surface being contoured to receive a syringe, said bottom surface being contoured to fit ergonomically within the hand of the operator.

15. The tissue sampling device as claimed in claim 13 wherein said button slide comprises an outer frame portion and an inner tab portion, said outer frame portion comprising a proximal end, a distal end, a pair of sides, and an interior cavity, said inner tab portion comprising a proximal end and a distal end, said proximal end of said inner tab portion being hingedly connected to said proximal end of said outer frame portion, said distal end of said inner tab portion being free and biased upwardly towards said slot in said cover, wherein said button is provided on top of said inner tab portion proximate to said distal end, whereby said button is biased upwardly through said slot but may be downwardly depressed.

16. The tissue sampling device as claimed in claim 15 wherein said cover further comprises a proximal notch and a distal notch and wherein said inner tab portion further comprises a pawl, said pawl being alternately releasably lockably retained in said proximal notch and in said distal notch and movable by depression of said button to alternately position said sampling needle in a retracted position wherein said distal tip of said sampling needle is disposed within said flexible catheter and in an extended position wherein said distal tip of said sampling needle extends distally beyond said distal end of said flexible catheter, respectively.

* * * * *

UNITED STATES PATENT AND TRADEMARK OFFICE
CERTIFICATE OF CORRECTION

PATENT NO. : 7,625,346 B2
APPLICATION NO. : 10/449826
DATED : December 1, 2009
INVENTOR(S) : Grigoryants et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 908 days.

Signed and Sealed this

Twenty-sixth Day of October, 2010

David J. Kappos
*Director of the United States Patent and Trademark Office*